(12) United States Patent
Beck et al.

(10) Patent No.: US 8,679,514 B2
(45) Date of Patent: Mar. 25, 2014

(54) FUNGICIDAL MIXTURES BASED ON AZOLOPYRIMIDINYLAMINES

(75) Inventors: Christine Beck, Speyer (DE); Matthias Niedenbrück, Limburgerhof (DE); Maria Scherer, Landau (DE); Reinhard Stierl, Freinsheim (DE); Siegfried Strathmann, Limburgerhof (DE); Udo Hünger, Mannheim (DE)

(73) Assignee: BASF SE, Ludwighsafen (DE)

( * ) Notice: Subject to any disclaimer, the term of this patent is extended or adjusted under 35 U.S.C. 154(b) by 1454 days.

(21) Appl. No.: 11/996,608

(22) PCT Filed: Jul. 20, 2006

(86) PCT No.: PCT/EP2006/064463
§ 371 (c)(1),
(2), (4) Date: Jan. 24, 2008

(87) PCT Pub. No.: WO2007/012598
PCT Pub. Date: Feb. 1, 2007

(65) Prior Publication Data
US 2008/0234295 A1  Sep. 25, 2008

(30) Foreign Application Priority Data

Jul. 27, 2005  (DE) .......................... 10 2005 035 688

(51) Int. Cl.
| | | |
|---|---|---|
| A01N 43/90 | (2006.01) | |
| A01P 3/00 | (2006.01) | |
| A01N 59/20 | (2006.01) | |
| A01N 47/24 | (2006.01) | |
| A01N 47/14 | (2006.01) | |
| A01N 47/12 | (2006.01) | |
| A01N 47/04 | (2006.01) | |
| A01N 43/88 | (2006.01) | |
| A01N 43/76 | (2006.01) | |
| A01N 43/653 | (2006.01) | |
| A01N 43/54 | (2006.01) | |
| A01N 43/50 | (2006.01) | |
| A01N 43/40 | (2006.01) | |
| A01N 37/50 | (2006.01) | |
| A01N 37/46 | (2006.01) | |

(52) U.S. Cl.
USPC .................. 424/404; 514/259.31; 514/259.3; 504/100

(58) Field of Classification Search
USPC ........... 514/259.31, 259.3; 510/100; 424/404
See application file for complete search history.

(56) References Cited

U.S. PATENT DOCUMENTS

| | | | |
|---|---|---|---|
| 4,567,263 A | 1/1986 | Eicken et al. | |
| 4,617,303 A | 10/1986 | Eicken et al. | |
| 6,268,371 B1 | 7/2001 | Sieverding et al. | |
| 7,307,172 B2 | 12/2007 | Blasco et al. | |
| 2003/0078301 A1* | 4/2003 | Cohen et al. .................. | 514/561 |
| 2005/0261314 A1 | 11/2005 | i Blasco et al. | |
| 2007/0167463 A1 | 7/2007 | Blasco et al. | |
| 2007/0173408 A1 | 7/2007 | Blasco et al. | |
| 2007/0179061 A1 | 8/2007 | Blasco et al. | |

FOREIGN PATENT DOCUMENTS

| | | |
|---|---|---|
| EP | 0 071 792 | 1/1985 |
| EP | 141317 | 5/1985 |
| EP | 0 988 790 | 5/2003 |
| WO | WO 03/009687 | 2/2003 |
| WO | WO 2005/032249 | 4/2005 |
| WO | WO 2005/087771 | 9/2005 |
| WO | WO 2005/087772 | 9/2005 |
| WO | WO 2005/087773 | 9/2005 |

OTHER PUBLICATIONS

English language translation of the International Preliminary Report on Patentability issued Feb. 26, 2008, in corresponding International Application No. PCT/EP2006/064463.

* cited by examiner

Primary Examiner — Kortney L Klinkel
(74) Attorney, Agent, or Firm — Brinks Gilson & Lione

(57) ABSTRACT

Fungicidal mixtures comprising, as active components,
1) azolopyrimidinylamines of the formula I,

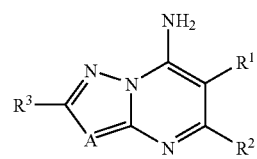

in which the substituents are as defined in the description and
2) at least one active compound II selected from the following groups: azoles, strobilurins, carboxamides, heterocylic compounds, carbamates and other active compounds selected from the group consisting of guanidines, antibiotics, sulfur-containing heterocyclyl compounds, organophosphorus compounds, organochlorine compounds, inorganic active compounds, growth retardants and cyflufenamid, cymoxanil, dimethirimol, ethirimol, furalaxyl, metrafenone and spiroxamine;
in a synergistically effective amount.
Methods for controlling harmful fungi using mixtures of the compound I with active compounds II and the use of the compound I with active compounds II for preparing such mixtures, and also compositions comprising these mixtures.

11 Claims, No Drawings

FUNGICIDAL MIXTURES BASED ON AZOLOPYRIMIDINYLAMINES

This application is a National Stage application of International Application No. PCT/EP2006/064463 filed Jul. 20, 2006, the entire contents of which is hereby incorporated herein by reference. This application also claims the benefit under 35 U.S.C. §119 of German Patent Application No. 102005035688.5, filed Jul. 27, 2005.

DESCRIPTION

The present invention relates to fungicidal mixtures comprising, as active components,
1) azolopyrimidinylamines of the formula I,

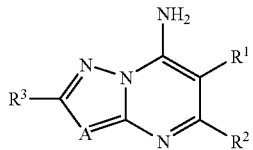

in which the substituents are as defined below:
$R^1$ is $C_3$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;
$R^2$ is $C_1$-$C_{12}$-alkyl, $C_2$-$C_{12}$-alkenyl, $C_1$-$C_4$-haloalkyl, $C_1$-$C_4$-alkoxy-$C_1$-$C_4$-alkyl;
where the aliphatic chains in $R^1$ and/or $R^2$ may be substituted by one to four identical or different groups $R^a$:
$R^a$ is halogen, cyano, hydroxyl, mercapto, $C_1$-$C_{10}$-alkyl, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^A R^B$;
$R^A$, $R^B$ are hydrogen and $C_1$-$C_6$-alkyl;
where the cyclic groups in $R^1$ and/or $R^a$ may be substituted by one to four groups $R^b$:
$R^b$ is halogen, cyano, hydroxyl, mercapto, nitro, $NR^A R^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy;
$R^3$ is hydrogen, halogen, cyano, $NR^A R^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkylcarbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio, $C_1$-$C_6$-alkyl-$S(O)_m$—;
m is 0, 1 or 2;
A is CH or N;
and
2) at least one active compound II selected from the following groups:
A) azoles, such as bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole;
prochloraz, pefurazoate, imazalil, triflumizole, cyazofamid;
benomyl, carbendazim, thiabendazole, fuberidazole;
ethaboxam, etridiazole, hymexazole;

B) strobilurins, such as azoxystrobin, dimoxystrobin, enestroburin, fluoxastrobin, kresoxim-methyl, metominostrobin, orysastrobin, picoxystrobin, pyraclostrobin, trifloxystrobin, or methyl (2-chloro-5-[1-(3-methylbenzyl-oxyimino)ethyl]benzyl)carbamate,
methyl (2-chloro-5-[1-(6-methylpyridin-2-ylmethoxyimino)ethyl]benzyl)carbamate, methyl 2-(ortho-((2,5-di-methylphenyloxymethylene)phenyl)-3-methoxyacrylate;

C) carboxamides, such as carboxin, benalaxyl, boscalid, fenhexamid, flutolanil, furametpyr, mepronil, metalaxyl, mefenoxam, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide;
3,4-dichloro-N-(2-cyanophenyl)isothiazol-5-carboxamide;
dimethomorph, flumorph;
flumetover, fluopicolide (picobenzamid), zoxamide;
carpropamid, diclocymet, mandipropamid;
N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)-prop-2-ynyloxy]-3-methoxyphenyl}ethyl)-2-ethanesulfonylamino-3-methyl-butyramide;

D) heterocylic compounds, such as fluazinam, pyrifenox;
bupirimate, cyprodinil, fenarimol, ferimzone, mepanipyrim, nuarimol,
pyrimethanil;
triforine;
fenpiclonil, fludioxonil;
aldimorph, dodemorph, fenpropimorph, tridemorph;
fenpropidin, iprodione, procymidone, vinclozolin;
famoxadone, fenamidone, octhilinone, probenazole;
amisulbrom, anilazine, diclomezine, pyroquilon, proquinazid, tricyclazole;
5-chloro-7-(4-methylpiperidin-1-yl)-6-(2,4,6-trifluorophenyl)-[1,2,4]triazolo[1,5-a]pyrimidine,
2-butoxy-6-iodo-3-propylchromen-4-one; acibenzolar-5-methyl, captafol, captan, dazomet, folpet, fenoxanil, quinoxyfen; 3-[5-(4-chlorophenyl)-2,3-dimethyl-isoxazolidin-3-yl]pyridine;

E) carbamates, such as mancozeb, maneb, metam, metiram, ferbam, propineb, thiram, zineb, ziram;
diethofencarb, iprovalicarb, flubenthiavalicarb, propamocarb;
methyl 3-(4-chlorophenyl)-3-(2-isopropoxycarbonylamino-3-methyl-butyrylamino)propanoate;
and
F) other active compounds, such as
guanidines: dodine, iminoctadine, guazatine;
antibiotics: kasugamycin, streptomycin, polyoxine, validamycin A;
nitrophenyl derivates: binapacryl, dinocap, dinobuton;
sulfur-containing heterocyclyl compounds: dithianon, isoprothiolane;
organometal compounds: fentin salts, such as fentinacetate;

organophosphorus compounds: edifenphos, iprobenfos, fosetyl, fosetyl-aluminum, phosphorous acid and its salts, pyrazophos, tolclofos-methyl;

organochlorine compounds: chlorothalonil, dichlofluanid, flusulfamide, hexachlorobenzene, phthalide, pencycuron, quintozene, thiophanate-methyl, tolylfluanid;

inorganic active compounds: Bordeaux mixture, copper acetate, copper hydroxide, copper oxychloride, basic copper sulfate, sulfur;

others: cyflufenamid, cymoxanil, dimethirimol, ethirimol, furalaxyl, metrafenone and spiroxamine;

growth retardants: prohexadione and its salts, trinexapac-ethyl, chlormequat, mepiquat-chloride and diflufenzopyr;

in a synergistically effective amount.

Moreover, the invention relates to a method for controlling harmful fungi using mixtures of the compound I with active compounds II and to the use of the compound I with active compounds II for preparing such mixtures, and also to compositions comprising these mixtures.

The azolopyrimidin-7-ylamines of the formula I referred to above as component 1, their preparation and their action against harmful fungi are known from the literature (EP-A 71 792; EP-A 141 317; WO 03/009687; WO 05/087771; WO 05/087772; WO 05/087773; PCT/EP/05/002426; PCT/EP2006/050922; PCT/EP2006/060399.

The active compounds II mentioned above as component 2, their preparation and their action against harmful fungi are generally known; they are commercially available.

bitertanol, β-([1,1'-biphenyl]-4-yloxy)-α-(1,1-dimethylethyl)-1H-1,2,4-triazole-1-ethanol (DE 23 24 020), bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4] triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorphenyl)-2-(2-propenyloxy)ethyl]-1H-imidazole (Fruits, 1973, Vol. 28, p. 545);

epoxiconazole, (2RS,3 SR)-1-[3-(2-chlorophenyl)-2,3-epoxy-2-(4-fluorophenyl)propyl]-1H-1,2,4-triazole (EP-A 196 038);

fluquinconazole, 3-(2,4-dichlorophenyl)-6-fluoro-2-[1,2,4]-triazol-1-yl-3H-quinazolin-4-one (Proc. Br. Crop Prot. Conf. Pests Dis., 5-3, 411 (1992));

fenbuconazole, α-[2-(4-chlorophenyl)ethyl]-α-phenyl-1H-1,2,4-triazole-1-propanenitrile (Proc. 1988 Br. Crop Prot. Conf.—Pests Dis. Vol. 1, p. 33);

flusilazole, 1-{[bis-(4-fluorophenyl)methylsilanyl]methyl}-1H-[1,2,4]triazole (Proc. Br. Crop Prot. Conf.—Pests Dis., 1, 413 (1984));

flutriafol, α-(2-fluorophenyl)-α-(4-fluorophenyl)-1H-1,2,4-triazole-1-ethanol (EP 15 756);

hexaconazole, 2-(2,4-dichlorophenyl)-1-[1,2,4]triazol-1-yl-hexan-2-ol (CAS RN 79983-71-4);

imibenconazole, (4-chlorophenyl)methyl N-(2,4-dichlorophenyl)-1H-1,2,4-triazole-1-ethanimidothioate ((Proc. 1988 Br. Crop Prot. Conf.—Pests Dis. Vol. 2, p. 519), imidothioate ((Proc. 1988 Br. Crop Prot. Conf.—Pests Dis. Vol. 2, p. 519), ipconazole, 2-[(4-chlorophenyl)methyl]-5-(1-methylethyl)-1-(1H-1,2,4-triazol-1-yl-methyl)cyclopentanol (EP 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4] triazole (Pesticide Manual, 12th Ed. (2000), p. 712);

propiconazole, 1-[[2-(2,4-dichlorophenyl)-4-propyl-1,3-dioxolan-2-yl]methyl]-1H-1,2,4-triazole (BE 835 579);

prothioconazole, 2-[2-(1-chlorocyclopropyl)-3-(2-chlorophenyl)-2-hydroxypropyl]-2,4-dihydro-[1,2,4]triazole-3-thione (WO 96/16048);

simeconazole, α-(4-fluorophenyl)-α-[(trimethylsilyl)methyl]-1H-1,2,4-triazole-1-ethanol [CAS RN149508-90-7], triadimefon, 1-(4-chlorophenoxy)-3,3-dimethyl-1-(1H-1,2,4-triazol-1-yl)-2-butanone;

triadimenol, β-(4-chlorophenoxy)-α-(1,1-dimethylethyl)-1H-1,2,4-triazole-1-ethanol;

tebuconazole, 1-(4-chlorophenyl)-4,4-dimethyl-3-[1,2,4] triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP 234 242);

triticonazole, (5E)-5-[(4-chlorophenyl)methylene]-2,2-dimethyl-1-(1H-1,2,4-triazol-1-ylmethyl)cyclopentanol (FR 26 41 277);

prochloraz, N-{propyl-[2-(2,4,6-trichlorophenoxy)ethyl]}imidazole-1-carboxamide (U.S. Pat. No. 3,991,071);

pefurazoate, 4-pentenyl 2-[(2-furanylmethyl)(1H-imidazol-1-ylcarbonyl)amino]butanoate [CAS RN 101903-30-4], triflumizole, (4-chloro-2-trifluoromethylphenyl)-(2-propoxy-1-[1,2,4]triazol-1-ylethylidene)amine (JP-A 79/119 462)

cyazofamid, 4-chloro-2-cyano-N,N-dimethyl-5-(4-methylphenyl)-1H-imidazole-1-sulfon-amide (CAS RN 120116-88-3], benomyl, N-butyl-2-acetylaminobenzoimidazol-1-carboxamide (U.S. Pat. No. 3,631,176);

carbendazim, methyl (1H-benzoimidazol-2-yl)-carbamate (U.S. Pat. No. 3,657,443);

thiabendazole, 2-(1,3-thiazol-4-yl)benzimidazole (U.S. Pat. No. 3,017,415), fuberidazole, 2-(2-furanyl)-1H-benzimidazole (DE 12 09 799), ethaboxam, N-(cyano-2-thienylmethyl)-4-ethyl-2-(ethylamino)-5-thiazolcarboxamide (EP-A 639 574), etridiazole, hymexazole, 5-methyl-1,2-oxazol-3-ol (JP 518249, JP 532202), azoxystrobin, methyl 2-{2-[6-(2-cyano-1-vinylpenta-1,3-dienyloxy)pyrimidin-4-yloxy]phenyl}-3-methoxyacrylate (EP-A 382 375), dimoxystrobin, (E)-2-(methoxyimino)-A-methyl-2-[α-(2,5-xylyloxy)-o-tolyl]acetamide (EP-A 477 631);

fluoxastrobin, (E)-{2-[6-(2-chlorophenoxy)-5-fluoropyrimidin-4-yloxy]phenyl}(5,6-dihydro-1,4,2-dioxazin-3-yl) methanone O-methyloxime (WO 97/27189);

kresoxim-methyl, methyl(E)-methoxyimino[α-(o-tolyloxy)-o-tolyl]acetate (EP-A 253 213);

metominostrobin, (E)-2-(methoxyimino)-N-methyl-2-(2-phenoxyphenyl)acetamide (EP-A 398 692);

orysastrobin, (2E)-2-(methoxyimino)-2-{2-[(3E,5E6E)-5-(methoxyimino)-4,6-dimethyl-2,8-dioxa-3,7-diazanona-3,6-dien-1-yl]phenyl}-N-methylacetamide (WO 97/15552);

picoxystrobin, methyl 3-methoxy-2-[2-(6-trifluoromethylpyridin-2-yloxymethyl)phenyl]-acrylate (EP-A 278 595);

pyraclostrobin, methyl N-{2-[1-(4-chlorophenyl)-1-pyrazol-3-yloxymethyl]phenyl}(N-methoxy)carbamate (WO-A 96/01256);

trifloxystrobin, methyl(E)-methoxyimino-{(E)-α-[1-(α,α,α-trifluoro-m-tolyl)ethylidene-aminooxy]-o-tolyl}acetate (EP-A 460 575);

carboxin, 5,6-dihydro-2-methyl-N-phenyl-1,4-oxathiin-3-carboxamide (U.S. Pat. No. 3,249,499), benalaxyl, methyl N-(phenylacetyl)-N-(2,6-xylyl)-DL-alaninate (DE 29 03 612), boscalid, 2-chloro-N-(4'-chlorbiphenyl-2-yl)nicotinamide (EP-A 545 099);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

flutolanil, α,α,α-trifluoro-3'-isopropoxy-o-toluanilide (JP 1104514), furametpyr, 5-chloro-N-(1,3-dihydro-1,1,3-trimethyl-4-isobenzofuranyl)-1,3-dimethyl-1H-pyrazole-4-carboxamide [CAS RN 123572-88-3], mepronil, 3'-isopropoxy-o-toluanilide (U.S. Pat. No. 3,937, 840), metalaxyl, methyl N-(methoxyacetyl)-N-(2,6-xylyl)-DL-alaninate (GB 15 00 581);

mefenoxam, methyl N-(2,6-dimethylphenyl)-N-(methoxyacetyl)-D-alaninate;

ofurace, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059), oxycarboxin, 5,6-dihydro-2-methyl-1,4-oxathiin-3-carboxanilide 4,4-dioxide (U.S. Pat. No. 3,399,214), penthiopyrad, N-[2-(1,3-dimethylbutyl)-3-thienyl]-1-methyl-3-(trifluoromethyl)-1H-pyrazole-4-carboxamide (JP 10130268), thifluzamide, N-[2,6-dibromo-4-(trifluoromethoxy)phenyl]-2-methyl-4-(trifluoromethyl)-5-thiazolecarboxamide;

tiadinil, 3'-chloro-4,4'-dimethyl-1,2,3-thiadiazole-5-carboxanilide [CAS RN 223580-51-6], dimethomorph, 3-(4-chlorophenyl)-3-(3,4-dimethoxyphenyl)-1-morpholin-4-ylpropenone (EP-A 120 321);

flumorph, 3-(4-fluorophenyl)-3-(3,4-dimethoxyphenyl)-1-morpholin-4-ylpropenone (EP-A 860 438);

flumetover, 2-(3,4-dimethoxyphenyl)-N-ethyl-α,α,α-trifluoro-N-methyl-p-toluamide [AGROW No. 243, 22 (1995)], fluopicolide (picobenzamid), 2,6-dichloro-N-(3-chloro-5-trifluoromethylpyridin-2-ylmethyl)benzamide (WO 99/42447);

zoxamide, (RS)-3,5-dichloro-N-(3-chloro-1-ethyl-1-methyl-2-oxopropyl)-p-toluamide [CAS RN 156052-68-5];

carpropamid, 2,2-dichloro-N-[1-(4-chlorophenyl)ethyl]-1-ethyl-3-methylcyclopropane-carboxamide [CAS RN 104030-54-8], diclocymet, 2-cyano-N-[(1R)-1-(2,4-dichlorophenyl)ethyl]-3,3-dimethyl butanamide;

mandipropamid, (RS)-2-(4-chlorophenyl)-N-[3-methoxy-4-(prop-2-ynyloxy)phenethyl]-2-(prop-2-ynyloxy)acetamide [CAS RN 374726-62-2];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

pyrifenox, 1-(2,4-dichlorophenyl)-2-(3-pyridinyl)ethanone O-methyloxime (EP-A 49 854);

bupirimate, 5-butyl-2-ethylamino-6-methylpyrimidin-4-yi-dimethylsulfamate [CAS RN 41483-43-6];

cyprodinil, (4-cyclopropyl-6-methylpyrimidin-2-yl)phenylamine (EP-A 310 550);

fenarimol, (4-chlorophenyl) (2-chlorophenyl)pyrimidin-5-ylmethanol (GB 12 18 623);

ferimzone, (2)-2'-methylacetophenone 4,6-dimethylpyrimidin-2-ylhydrazone [CAS RN 89269-64-7];

mepanipyrim, (4-methyl-6-prop-1-ynylpyrimidin-2-yl)phenylamine (EP-A 224 339);

nuarimol, α-(2-chlorophenyl)-α-(4-fluorophenyl)-5-pyrimidinemethanol (GB 12 18 623);

pyrimethanil, 4,6-dimethylpyrimidin-2-ylphenylamine (DD-A 151 404);

triforine, N,N-{piperazine-1,4-diylbis[(trichloromethyl)methylene]}diformamide (DE 19 01 421);

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482);

aldimorph, 4-alkyl-2,5(or 2,6)-dimethylmorpholine, comprising 65-75% of 2,6-dimethyl-morpholine and 25-35% of 2,5-dimethylmorpholine, comprising more than 85% of 4-dodecyl-2,5(or 2,6)-dimethylmorpholine, where "alkyl" may also include octyl, decyl, tetradecyl or hexadecyl and where the cis/trans ratio is 1:1;

dodemorph, 4-cyclododecyl-2,6-dimethylmorpholine (DE 1198125);

fenpropimorph, (RS)-cis-4-[3-(4-tert-butylphenyl)-2-methylpropyl]-2,6-dimethyl-morpholine (DE 27 52 096);

tridemorph, 2,6-dimethyl-4-tridecylmorpholine (DE 11 64 152); fenpropidin, (RS)-1-[3-(4-tert-butylphenyl)-2-methylpropyl]piperidine (DE 27 52 096);

iprodione, N-isopropyl-3-(3,5-dichlorophenyl)-2,4-dioxoimidazolidine-1-carboxamide (GB 13 12 536);

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-OS 22 07 576);

famoxadone, (RS)-3-anilino-5-methyl-5-(4-phenoxyphenyl)-1,3-oxazolidine-2,4-dione;

fenamidone, (S)-1-anilino-4-methyl-2-methylthio-4-phenylimidazolin-5-one;

octhilinone, probenazole, 3-allyloxy-1,2-benzothiazole 1,1-dioxide;

amisulbrom, N,N-dimethyl-3-(3-bromo-6-fluoro-2-methylindole-1-sulfonyl)-[1,2,4]triazole-1-sulfonamide (WO 03/053145);

anilazine, 4,6-dichloro-N-(2-chlorophenyl)-1,3,5-triazine-2-amine (U.S. Pat. No. 2,720,480);

diclomezine, 6-(3,5-dichlorophenyl)-p-tolyl)pyridazin-3(2H)-one;

pyroquilon, proquinazid, 6-iodo-2-propoxy-3-propylquinazolin-4(3H)-one (WO 97/48684);

tricyclazole, 5-methyl-1,2,4-triazolo[3,4-b]benzothiazole (GB 14 19 121);

acibenzolar-5-methyl, methyl benzo[1,2,3]thiadiazole-7-carbothionate;

captafol, N-(1,1,2,2-tetrachloroethylthio)cyclohex-4-ene-1,2-dicarboximide;

captan, 2-trichloromethylsulfanyl-3a,4,7,7a-tetrahydroisoindole-1,3-dione (U.S. Pat. No. 2,553,770);

dazomet, 3,5-dimethyl-1,3,5-thiadiazinane-2-thione;
folpet, 2-trichloromethylsulfanylisoindole-1,3-dione (U.S. Pat. No. 2,553,770);
fenoxanil, N-(1-cyano-1,2-dimethylpropyl)-2-(2,4-dichlorophenoxy) propanamide;
quinoxyfen, 5,7-dichloro-4-(4-fluorophenoxy)quinoline (U.S. Pat. No. 5,240,940);
mancozeb, manganese ethylenebis(dithiocarbanate) zinc complex (U.S. Pat. No. 3,379,610);
maneb, manganese ethylenebis(dithiocarbamate) (U.S. Pat. No. 2,504,404);
metam, methyldithiocarbaminic acid (U.S. Pat. No. 2,791,605);
metiram, zinc ammoniate ethylenebis(dithiocarbamate) (U.S. Pat. No. 3,248,400);
propineb, zinc propylenebis(dithiocarbamate) polymer (BE 611 960);
ferbam, iron(3+) dimethyldithiocarbamate (U.S. Pat. No. 1,972,961);
thiram, bis(dimethylthiocarbamoyl) disulfide (DE 642 532);
ziram, dimethyldithiocarbamate;
zineb, zinc ethylenebis(dithiocarbamate) (U.S. Pat. No. 2,457,674);
diethofencarb, isopropyl 3,4-diethoxycarbanilate; iprovalicarb, isopropyl [(1S)-2-methyl-1-(1-p-tolylethylcarbamoyl)propyl]carbamate (EP-A 472 996);
flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323,984);
propamocarb, propyl 3-(dimethylamino)propylcarbamate (DE 16 43 040);
dodine, (2,4-dichlorophenoxy)acetic acid (U.S. Pat. No. 2,867,562);
iminoctadine, bis(8-guanidinooctyl)amine (GB 11 14 155);
guazatine, mixture of products from the amidation of iminodi (octamethylene)diamine, mainly iminoctadine;
kasugamycin, 1 L-1,3,4/2,5,6-1-deoxy-2,3,4,5,6-pentahydroxycyclohexyl 2-amino-2,3,4,6-tetradeoxy-4-(α-iminoglycino)-α-D-arabino-hexopyranoside;
streptomycin, O-2-deoxy-2-methylamino-α-L-glucopyranosyl-(1-2)-C-5-deoxy-3-1-formyl-α-L-lyxofuranosyl-(1→4)-N$^1$,N$^3$-diamidino-D-streptamine;
polyoxins, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid and the salts thereof;
validamycin A,
binapacryl, (RS)-2-sec-butyl-4,6-dinitrophenyl 3-methylcrotonate; dinocap, the mixture of 2,6-dinitro-4-octylphenyl crotonate and 2,4-dinitro-6-octylphenyl crotonate, wherein "octyl" is a mixture of 1-methylheptyl, 1-ethylhexyl and 1-propylpentyl (U.S. Pat. No. 2,526,660);
dinobuton, (RS)-2-sec-butyl-4,6-dinitrophenyl isopropyl carbonate;
dithianon, 5,10-dioxo-5,10-dihydronaphtho[2,3-b][1,4]dithiin-2,3-dicarbonitrile (GB 857 383);
isoprothiolane, indol-3-ylacetic acid;
fentin acetate, triphenyltin acetate (U.S. Pat. No. 3,499,086);
edifenphos, O-ethyl S,S-diphenyl phosphorodithioate;
iprobenfos, S-benzyl O,O-diisopropyl phosphorothioate (Jpn. Pesticide Inf., No. 2, S. 11 (1970));
fosetyl, fosetyl-aluminum, (aluminum) ethylphosphonate (FR 22 54 276);
pyrazophos, ethyl 2-diethoxyphosphinothioyloxy-5-methylpyrazolo[1,5-a]pyrimidine-6-carboxylate (DE 15 45 790);
tolclofos-methyl, O-2,6-dichloro-p-tolyl O,O-dimethyl phosphorothioate (GB 14 67 561);
chlorothalonil, 2,4,5,6-tetrachloroisophthalonitrile (U.S. Pat. No. 3,290,353);
dichlofluanid, N-dichlorofluoromethylthio-N,N-dimethyl-N-phenylsulfamide (DE 11 93498);
flusulfamide, 2',4-dichloro-α,α,α-trifluoro-4'-nitro-m-toluenesulfanilide (EP-A 199 433);
hexachlorobenzene (C. R. Seances Acad. Agric. Fr., Vol. 31, p. 24 (1945));
phthalide (DE 16 43 347);
pencycuron, 1-(4-chlorobenzyl)-1-cyclopentyl-3-phenylurea (DE 27 32 257);
quintozene, pentachloronitrobenzene (DE 682 048);
thiophanate-methyl, 1,2-phenylenebis(iminocarbonothioyl) bis(dimethylcarbamate) (DE-OS 19 30 540);
tolylfluanid, N-dichlorofluoromethylthio-N,N-dimethyl-N-p-tolylsulfamide (DE 11 93 498);
Bordeaux mixture, mixture of calcium hydroxide and copper (II) sulfate;
copper hydroxide, $Cu(OH)_2$; copper oxychloride, $Cu_2Cl(OH)_3$;
cyflufenamid, (Z)-N-[α-(cyclopropylmethoxyimino)-2,3-difluoro-6-(trifluoromethyl)benzyl]-2-phenylacetamide (WO 96/19442);
cymoxanil, 1-(2-cyano-2-methoxyiminoacetyl)-3-ethylurea (U.S. Pat. No. 3,957,847);
dimethirimol, 5-butyl-2-dimethylamino-6-methylpyrimidin-4-ol (GB 11 82 584);
ethirimol, 5-butyl-2-ethylamino-6-methylpyrimidin-4-ol (GB 11 82 584);
furalaxyl, methyl N-(2-furoyl)-N-(2,6-xylyl)-DL-alaninate (GB 14 48 810);
metrafenone, 3'-bromo-2,3,4,6'-tetramethoxy-2',6-dimethylbenzophenone (U.S. Pat. No. 5,945,567);
spiroxamine, (8-tert-butyl-1,4-dioxaspiro[4.5]dec-2-yl)diethylamine (EP-A 281 842).

The compounds named according to IUPAC, their preparation and their fungicidal action are likewise known:
methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate (EP-A 12 01 648);
methyl 2-(ortho-((2,5-dimethylphenyloxymethylene)phenyl)-3-methoxyacrylate (EP-A 226 917);
5-chloro-7-(4-methylpiperidin-1-yl)-6-(2,4,6-trifluorophenyl)-[1,2,4]triazolo[1,5-a]pyrimidine (WO 98/46608),
3,4-dichloro-N-(2-cyanophenyl)isothiazole-5-carboxamide (WO 99/24413),
N-(2-{4-[3-(4-chlorophenyl)prop-2-ynyloxy]-3-methoxyphenyl}ethyl)-2-methanesulfonyl-amino-3-methylbutyramide, N-(2-{4-[3-(4-chlorophenyl)prop-2-ynyloxy]-3-methoxyphenyl}ethyl)-2-ethanesulfonylamino-3-methylbutyramide (WO 04/049804,
N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide (WO 03/066609), N-(3',4'-dichloro-5-fluorobiphenyl-2-yl)-3-difluoromethyl-1-methylpyrazole-4-carboxamide (WO 03/053145);
2-butoxy-6-iodo-3-propylchromen-4-one (WO 03/14103), 3-[5-(4-chlorophenyl)-2,3-dimethylisoxazolidin-3-yl]pyridine (EP-A 10 35 122);

amisulbrom, N,N-dimethyl-3-(3-bromo-6-fluoro-2-methylindole-1-sulfonyl)-[1,2,4]triazole-1-sulfonamide (WO 03/053145), methyl 3-(4-chlorophenyl)-3-(2-isopropoxycarbonylamino-3-methylbutyrylamino)-propanoate (EP-A 1028125).

It is an object of the present invention, with a view to reducing the application rates and broadening the activity spectrum of the known compounds, to provide mixtures which, at a reduced total amount of active compounds applied, have improved activity against harmful fungi, in particular for certain indications.

We have found that this object is achieved by the mixtures defined at the outset. Moreover, we have found that simultaneous, that is joint or separate, application of the compounds I and an active compound II or successive application of the compounds I and an active compound II allows better control of harmful fungi than is possible with the individual compounds (synergistic mixtures). The compounds I can be used as a synergist for a large number of different active compounds. The simultaneous, that is joint or separate, application of the compound I with an active compound II increases the fungicidal activity in a superadditive manner.

The mixtures of the compounds I and an active compound II or the simultaneous, that is joint or separate, use of the compounds I and an active compound II are/is distinguished by excellent activity against a broad spectrum of phytopathogenic fungi, in particular from the classes of the Ascomycetes, Deuteromycetes, Oomycetes and Basidiomycetes. Some of them are systemically active and can be used in crop protection as foliar fungicides, as fungicides for seed dressing and as soil fungicides.

They are particularly important in the control of a multitude of fungi on various crop plants, such as bananas, cotton, vegetables (for example cucumbers, beans and cucurbits), barley, grass, oats, coffee, potatoes, corn, fruit, rice, rye, soybeans, tomatoes, grape vines, wheat, ornamental plants, sugar cane and a multiplicity of seeds.

Advantageously, they are suitable for controlling the following plant diseases:

*Alternaria* species on vegetables, oilseed rape, sugar beet and fruit and rice, such as, for example, *A. solani* or *A. alternata* on potatoes and tomatoes;

*Aphanomyces* species on sugar beet and vegetables;

*Ascochyta* species on cereals and vegetables;

*Bipolaris* and *Drechslera* species on corn, cereals, rice and lawns, such as, for example, *D. maydison* corn;

*Blumeria graminis* (powdery mildew) on cereals;

*Botrytis cinerea* (gray mold) on strawberries, vegetables, flowers and grapevines;

*Bremia lactucae* on lettuce;

*Cercospora* species on corn, soybeans, rice and sugar beet;

*Cochliobolus* species on corn, cereals, rice, such as, for example, *Cochliobolus sativus* on cereals, *Cochliobolus miyabeanus* on rice;

Colletotricum species on soybeans and cotton;

*Drechslera* species, *Pyrenophora* species on corn, cereals, rice and lawns, such as, for example, *D. teres* on barley or *D. tritici-repentis* on wheat;

*Esca* on grapevines, caused by *Phaeoacremonium chlamydosporium, Ph. Aleophilum* and *Formitipora punctata* (syn. *Phellinus punctatus*),

*Exserohilum* species on corn;

*Eiysiphe cichoracearum* and *Sphaerotheca fuliginea* on cucumbers;

*Fusarium* and *Verticillium* species on various plants, such as, for example, *F. graminearum* or *F. culmorum* on cereals or *F. oxysporum* on a multitude of plants, such as, for example, tomatoes;

*Gaeumanomyces* graminis on cereals;

*Gibberella* species on cereals and rice (for example *Gibberella fujikurolon* rice);

Grainsfaining complex on rice;

*Helminthosporium* species on corn and rice;

*Michrodochium nivale* on cereals;

*Mycosphaerella* species on cereals, bananas and groundnuts, such as, for example, *M. graminicola* on wheat or *M. fijensis* on bananas;

*Peronospora* species on cabbage and bulbous plants, such as, for example, *P. brassicae* on cabbage or *P. destructoron* onions;

*Phakopsara pachyrhizi* and *Phakopsara meibomiae* on soybeans;

*Phomopsis* species on soybeans and sunflowers;

*Phytophthora infestans* on potatoes and tomatoes;

*Phytophthora* species on various plants, such as, for example, *P. capsici* on bell pepper;

*Plasmopara viticola* on grapevines;

*Podosphaera leucotricha* on apples;

*Pseudocercosporella herpotrichoides* on cereals;

*Pseudoperonospora* on various plants, such as, for example, *P. cubensis* on cucumber or *P. humili* on hops;

*Puccinia* species on various plants, such as, for example, *P. triticina, P. striformins, P. hordei* or *P. graminis* on cereals or *P. asparagion* asparagus;

*Pyricularia oryzae, Corticium sasakii, Sarocladium oryzae, S. affenuatum, Entyloma oryzae* on rice;

*Pyricularia grisea* on lawns and cereals;

*Pythium* spp. on lawns, rice, corn, cotton, oilseed rape, sunflowers, sugar beet, vegetables and other plants, such as, for example, *P. ultimum* on various plants, *P. aphanidermatum* on lawns;

*Rhizoctonia* species on cotton, rice, potatoes, lawns, corn, oilseed rape, potatoes, sugar beet, vegetables and on various plants, such as, for example, *R. solani* on beet and various plants;

*Rhynchosporium secalis* on barley, rye and triticale;

*Sclerotinia* species on oilseed rape and sunflowers;

*Septoria tritici* and *Stagonospora nodorum* on wheat;

*Erysiphe* (syn. *Uncinula*) *necator* on grapevines;

*Setospaeria* species on corn and lawns;

*Sphacelotheca reilinia* on corn;

*Thievaliopsis* species on soybeans and cotton;

*Tilletia* species on cereals;

*Ustilago* species on cereals, corn and sugar cane, such as, for example, *U. maydis* on corn;

*Venturia* species (scab) on apples and pears, such as, for example, *V. inaequalis* on apples.

The mixtures of the compounds I and active compounds II are suitable in particular for controlling harmful fungi from the class of the *Peronosporomycetes* (syn. Oomycetes), such as *Peronospora* species, *Phytophthora* species, *Plasmopara vificola* and *Pseudoperonospora* species, in particular fungi corresponding to those mentioned above.

The compounds I and active compounds II can be applied simultaneously, that is jointly or separately, or in succession, the sequence, in the case of separate application, generally not having any effect on the result of the control measures.

In the definitions of the symbols given for the formulae above, collective terms were used which generally represent the following substituents:

halogen: fluorine, chlorine, bromine and iodine;

alkyl: saturated straight-chain or branched hydrocarbon radicals having 1 to 4, 6, 8 or 10 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-me-thylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dime-thylbutyl, 3,3-dimethylbutyl, 1-ethylbutyl, 2-ethylbutyl, 1,1,2-trimethylpropyl, 1,2,2-tri-methylpropyl, 1-ethyl-1-methylpropyl and 1-ethyl-2-methylpropyl;

haloalkyl: straight-chain or branched alkyl groups having 1 to 2, 4 or 6 carbon atoms (as mentioned above), where some or all of the hydrogen atoms in these groups may be replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

With a view to the intended use of the azolopyrimidinylamines of the formula I, particular preference is given to the following meanings of the substituents, in each case on their own or in combination:

Particularly suitable for the mixtures according to the invention are compounds of the formula I in which $R^1$ is straight-chain or branched $C_3$-$C_{12}$-alkyl or phenyl which may be substituted by one to three halogen or $C_1$-$C_4$-alkyl groups.

In one embodiment of the compounds of the formula I, group $R^a$ is absent.

A preferred embodiment relates to compounds of the formula I in which $R^1$ is straight-chain or branched $C_5$-$C_{10}$-alkyl, in particular ethyl, 3,5,5-trimethylhexyl, n-heptyl, n-octyl, n-nonyl and n-decyl.

A further embodiment relates to the compounds of the formula I in which $R^1$ is phenyl which is unsubstituted or substituted by one to four halogen, cyano, hydroxyl, mercapto, nitro, $NR^A R^B$, $C_1$-$C_{10}$-alkyl, $C_1$-$C_6$-haloalkyl, $C_2$-$C_6$-alkenyl, $C_2$-$C_6$-alkynyl and $C_1$-$C_6$-alkoxy groups.

Preferred compounds of the formula I are those in which $R^1$ is a substituted phenyl group which corresponds to a group G

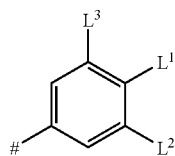

in which $L^1$ is cyano, halogen, hydroxyl, mercapto, nitro, $NR^A R^B$, $C_1$-$C_{10}$-alkyl, $C_1$-$C_6$-haloalkyl, $C_2$-$C_6$-alkenyl, $C_2$-$C_6$-alkynyl and $C_1$-$C_6$-alkoxy; and $L^2, L^3$ independently of one another are hydrogen or one of the groups mentioned under $L^1$ and # denotes the bond to the azolopyrimidine skeleton.

In a further embodiment of the compounds of the formula I, $L^1$ is cyano, halogen, hydroxyl, mercapto, nitro, $NR^A R^B$, $C_1$-$C_6$-alkyl, halomethyl or $C_1$-$C_2$-alkoxy, preferably cyano, halogen, $C_1$-$C_6$-alkyl, halomethyl or $C_1$-$C_2$-alkoxy.

In a further embodiment of the compounds of the formula I, $L^2$ is hydrogen or one of the groups mentioned above.

In a further embodiment of the compounds of the formula I, $L^3$ is hydrogen, cyano, halogen, hydroxyl, mercapto, nitro, $NR^A R^B$, $C_1$-$C_6$-alkyl, halomethyl or $C_1$-$C_2$-alkoxy, preferably hydrogen.

Preference is given to compounds of the formula I in which $R^2$ is straight-chain or branched $C_1$-$C_{12}$-alkyl, $C_1$-$C_4$-alkoxy-$C_1$-$C_4$-alkyl or $C_1$-$C_4$-haloalkyl.

In a particularly preferred embodiment of the compounds of the formula I, $R^2$ is methyl, ethyl, n-propyl, n-octyl, trifluoromethyl or methoxymethyl, in particular methyl, ethyl, trifluoromethyl or methoxymethyl.

Preference is furthermore given to compounds of the formula I in which $R^3$ is hydrogen.

In a further embodiment of the compounds of the formula I, $R^3$ is amino.

One embodiment of the compounds of the formula I relates to those in which A is N. These compounds correspond to the formula IA in which the variables are as defined for formula I:

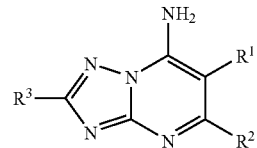

Another embodiment of the compounds of the formula I relates to those in which A is CH. These compounds correspond to the formula IB in which the variables are as defined for formula I:

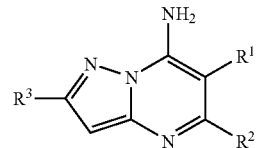

In a further embodiment of preferred compounds I, the carbon chains of $R^1$ and $R^2$ together do not have more than 12 carbon atoms.

Especially preferred with a view to their use are the compounds I compiled in the tables below. The groups mentioned for a substituent in the tables are furthermore per se, independently of the combination in which they are mentioned, a particularly preferred embodiment of the substituent in question.

Table 1

Compounds of the formula IA in which the combination of $R^1$, $R^2$ and $R^3$ for a compound corresponds in each case to one row of Table I Table 2

Compounds of the formula IB in which the combination of $R^1$, $R^2$ and $R^3$ for a compound corresponds in each case to one row of Table I

TABLE I

| No. | R¹ | R² | R³ |
|---|---|---|---|
| I-1 | C₆H₅ | CH₃ | H |
| I-2 | 2-Cl—C₆H₄ | CH₃ | H |
| I-3 | 3-Cl—C₆H₄ | CH₃ | H |
| I-4 | 4-Cl—C₆H₄ | CH₃ | H |
| I-5 | 2-F—C₆H₄ | CH₃ | H |
| I-6 | 3-F—C₆H₄ | CH₃ | H |
| I-7 | 4-F—C₆H₄ | CH₃ | H |
| I-8 | 2,4-Cl₂—C₆H₃ | CH₃ | H |
| I-9 | 3,4-Cl₂—C₆H₃ | CH₃ | H |
| I-10 | 2,4-F₂—C₆H₃ | CH₃ | H |
| I-11 | 3,4-F₂—C₆H₃ | CH₃ | H |
| I-12 | 4-CH₃—C₆H₄ | CH₃ | H |
| I-13 | 4-CH₂CH₃—C₆H₄ | CH₃ | H |
| I-14 | 4-CH₂CH₂CH₃—C₆H₄ | CH₃ | H |
| I-15 | 4-CH(CH₃)₂—C₆H₄ | CH₃ | H |
| I-16 | 4-CH₂CH₂CH₂CH₃—C₆H₄ | CH₃ | H |
| I-17 | 4-C(CH₃)CH₂CH₃—C₆H₄ | CH₃ | H |
| I-18 | 4-C(CH₃)₃—C₆H₄ | CH₃ | H |
| I-19 | CH₂CH₂CH₂CH₃ | CH₃ | H |
| I-20 | CH₂CH₂CH₂CH₂CH₃ | CH₃ | H |
| I-21 | CH₂CH₂CH₂CH₂CH₂CH₃ | CH₃ | H |
| I-22 | CH₂CH(CH₃)CH₂CH₂CH₃ | CH₃ | H |
| I-23 | CH₂CH(CH₂CH₃)₂ | CH₃ | H |
| I-24 | CH₂CH₂CH₂CH₂CH₂CH₂CH₃ | CH₃ | H |
| I-25 | CH₂CH₂CH₂CH₂CH₂CH₂CH₂CH₃ | CH₃ | H |
| I-26 | CH₂CH₂CH₂CH₂CH₂CH₂CH₂CH₂CH₃ | CH₃ | H |
| I-27 | CH₂CH₂CH₂CH₂CH₂CH₂CH₂CH₂CH₂CH₃ | CH₃ | H |
| I-28 | CH₂CH₂CH(CH₃)CH₂CH(CH₃)₃ | CH₃ | H |
| I-29 | CH₂CH₂CH₃ | CH₃ | NH₂ |
| I-30 | CH₂CH₂CH₂CH₃ | CH₃ | NH₂ |
| I-31 | CH₂CH₂CH₂CH₂CH₃ | CH₃ | NH₂ |
| I-32 | CH₂CH(CH₃)CH₂CH₂CH₃ | CH₃ | NH₂ |
| I-33 | CH₂CH(CH₂CH₃)₂ | CH₃ | NH₂ |
| I-34 | CH₂CH₂CH₂CH₂CH₂CH₂CH₃ | CH₃ | NH₂ |
| I-35 | CH₂CH₂CH₂CH₂CH₂CH₂CH₂CH₃ | CH₃ | NH₂ |
| I-36 | CH₂CH₂CH₂CH₂CH₂CH₂CH₂CH₂CH₃ | CH₃ | NH₂ |
| I-37 | CH₂CH₂CH₂CH₂CH₂CH₂CH₂CH₂CH₂CH₃ | CH₃ | NH₂ |
| I-38 | CH₂CH₂CH(CH₃)CH₂CH(CH₃)₃ | CH₃ | NH₂ |
| I-39 | CH₂CH₂CH₂CH₃ | CH₃ | CH₃ |
| I-40 | CH₂CH₂CH₂CH₂CH₃ | CH₃ | CH₃ |
| I-41 | CH₂CH₂CH₂CH₂CH₂CH₃ | CH₃ | CH₃ |
| I-42 | CH₂CH(CH₃)CH₂CH₂CH₃ | CH₃ | CH₃ |
| I-43 | CH₂CH(CH₂CH₃)₂ | CH₃ | CH₃ |
| I-44 | CH₂CH₂CH₂CH₂CH₂CH₂CH₃ | CH₃ | CH₃ |
| I-45 | CH₂CH₂CH₂CH₂CH₂CH₂CH₂CH₃ | CH₃ | CH₃ |
| I-46 | CH₂CH₂CH₂CH₂CH₂CH₂CH₂CH₂CH₃ | CH₃ | CH₃ |
| I-47 | CH₂CH₂CH₂CH₂CH₂CH₂CH₂CH₂CH₂CH₃ | CH₃ | CH₃ |
| I-48 | CH₂CH₂CH(CH₃)CH₂CH(CH₃)₃ | CH₃ | CH₃ |
| I-49 | (CH₂)₃—O—CH₃ | CH₃ | H |
| I-50 | (CH₂)₃—O—CH₂CH₃ | CH₃ | H |
| I-51 | (CH₂)₃—O—CH₂CH₂CH₃ | CH₃ | H |
| I-52 | (CH₂)₃—O—CH₂CH₂CH₂CH₃ | CH₃ | H |
| I-53 | (CH₂)₃—O—CH₂CH₂CH₂CH₂CH₃ | CH₃ | H |
| I-54 | (CH₂)₃—O—CH₂CH₂CH₂CH₂CH₂CH₃ | CH₃ | H |
| I-55 | (CH₂)₃—O—CH₂CH₂CH₂CH₂CH₂CH₂CH₃ | CH₃ | H |
| I-56 | (CH₂)₃—O—CH₂CH₂CH₂CH₂CH₂CH₂CH₂CH₃ | CH₃ | H |
| I-57 | (CH₂)₃—O—CH₂CH₂CH₂CH₂CH₂CH₂CH₂CH₂CH₃ | CH₃ | H |
| I-58 | (CH₂)₃—O—CH(CH₃)₂ | CH₃ | H |
| I-59 | (CH₂)₃—O—C(CH₃)₃ | CH₃ | H |
| I-60 | (CH₂)₃—O—CH₂C(CH₃)₃ | CH₃ | H |
| I-61 | (CH₂)₃—O—CH(CH₃)CH₂C(CH₃)₃ | CH₃ | H |
| I-62 | (CH₂)₃—O—CH(CH₂CH₃)CH₂C(CH₃)₃ | CH₃ | H |
| I-63 | (CH₂)₃—O—CH₂CH(CH₃)CH₂CH(CH₃)₂ | CH₃ | H |
| I-64 | (CH₂)₃—O—CH₂CH(CH₂CH₃)CH₂CH₂CH₃ | CH₃ | H |
| I-65 | (CH₂)₃—O—CH₂CH₂CH(CH₃)CH₂CH(CH₃)₂ | CH₃ | H |
| I-66 | (CH₂)₃—O—CH₂CH₂CH(CH₃)CH₂C(CH₃)₃ | CH₃ | H |
| I-67 | (CH₂)₃—O—CH₂CH₂CH(CH₃)CH₂CH₂CH(CH₃)₂ | CH₃ | H |
| I-68 | (CH₂)₃—O—CH₂CH₂CH(CH₃)CH₂CH₂CH₂CH(CH₃)₂ | CH₃ | H |
| I-69 | (CH₂)₃—O—CH₃ | CH₃ | CH₃ |
| I-70 | (CH₂)₃—O—CH₂CH₃ | CH₃ | CH₃ |
| I-71 | (CH₂)₃—O—CH₂CH₂CH₃ | CH₃ | CH₃ |
| I-72 | (CH₂)₃—O—CH₂CH₂CH₂CH₃ | CH₃ | CH₃ |
| I-73 | (CH₂)₃—O—CH₂CH₂CH₂CH₂CH₃ | CH₃ | CH₃ |
| I-74 | (CH₂)₃—O—CH₂CH₂CH₂CH₂CH₂CH₃ | CH₃ | CH₃ |
| I-75 | (CH₂)₃—O—CH₂CH₂CH₂CH₂CH₂CH₂CH₃ | CH₃ | CH₃ |
| I-76 | (CH₂)₃—O—CH₂CH₂CH₂CH₂CH₂CH₂CH₂CH₃ | CH₃ | CH₃ |
| I-77 | (CH₂)₃—O—CH₂CH₂CH₂CH₂CH₂CH₂CH₂CH₂CH₃ | CH₃ | CH₃ |
| I-78 | (CH₂)₃—O—CH(CH₃)₂ | CH₃ | CH₃ |

TABLE I-continued

| No. | R¹ | R² | R³ |
|---|---|---|---|
| I-79 | (CH₂)₃—O—C(CH₃)₃ | CH₃ | CH₃ |
| I-80 | (CH₂)₃—O—CH₂C(CH₃)₃ | CH₃ | CH₃ |
| I-81 | (CH₂)₃—O—CH(CH₃)CH₂C(CH₃)₃ | CH₃ | CH₃ |
| I-82 | (CH₂)₃—O—CH(CH₂CH₃)CH₂C(CH₃)₃ | CH₃ | CH₃ |
| I-83 | (CH₂)₃—O—CH₂CH(CH₃)CH₂CH(CH₃)₂ | CH₃ | CH₃ |
| I-84 | (CH₂)₃—O—CH₂CH(CH₂CH₃)CH₂CH₂CH₃ | CH₃ | CH₃ |
| I-85 | (CH₂)₃—O—CH₂CH₂CH(CH₃)CH₂CH(CH₃)₂ | CH₃ | CH₃ |
| I-86 | (CH₂)₃—O—CH₂CH₂CH(CH₃)CH₂C(CH₃)₃ | CH₃ | CH₃ |
| I-87 | (CH₂)₃—O—CH₂CH₂CH(CH₃)CH₂CH₂CH(CH₃)₂ | CH₃ | CH₃ |
| I-88 | (CH₂)₃—O—CH₂CH₂CH(CH₃)CH₂CH₂CH₂CH(CH₃)₂ | CH₃ | CH₃ |
| I-89 | CH₂—C₆H₅ | CF₃ | H |
| I-90 | CH₂-(4-Cl—C₆H₄) | CF₃ | H |
| I-91 | CH₂CH₂CH₃ | CF₃ | H |
| I-92 | CH₂CH₂CH₂CH₃ | CF₃ | H |
| I-93 | CH₂CH₂CH₂CH₂CH₃ | CF₃ | H |
| I-94 | CH₂CH₂CH₂CH₂CH₂CH₃ | CF₃ | H |
| I-95 | CH₂CH(CH₃)CH₂CH₂CH₃ | CF₃ | H |
| I-96 | CH₂CH(CH₂CH₃)₂ | CF₃ | H |
| I-97 | CH₂CH₂CH₂CH₂CH₂CH₂CH₃ | CF₃ | H |
| I-98 | CH₂CH₂CH₂CH₂CH₂CH₂CH₂CH₃ | CF₃ | H |
| I-99 | CH₂CH₂CH₂CH₂CH₂CH₂CH₂CH₂CH₃ | CF₃ | H |
| I-100 | CH₂CH₂CH₂CH₂CH₂CH₂CH₂CH₂CH₂CH₃ | CF₃ | H |
| I-101 | CH₂CH₂CH(CH₃)CH₂CH(CH₃)₃ | CF₃ | H |
| I-102 | cyclo-C₅H₉ | CF₃ | H |
| I-103 | cyclo-C₆H₁₁ | CF₃ | H |
| I-104 | CH₂CH₂CH₂CH₃ | CH₂CH₃ | H |
| I-105 | CH₂CH₂CH₂CH₂CH₃ | CH₂CH₃ | H |
| I-106 | CH₂CH₂CH₂CH₂CH₂CH₃ | CH₂CH₃ | H |
| I-107 | CH₂CH(CH₃)CH₂CH₂CH₃ | CH₂CH₃ | H |
| I-108 | CH₂CH(CH₂CH₃)₂ | CH₂CH₃ | H |
| I-109 | CH₂CH₂CH₂CH₂CH₂CH₂CH₃ | CH₂CH₃ | H |
| I-110 | CH₂CH₂CH₂CH₂CH₂CH₂CH₂CH₃ | CH₂CH₃ | H |
| I-111 | CH₂CH₂CH₂CH₂CH₂CH₂CH₂CH₂CH₃ | CH₂CH₃ | H |
| I-112 | CH₂CH₂CH₂CH₂CH₂CH₂CH₂CH₂CH₂CH₃ | CH₂CH₃ | H |
| I-113 | CH₂CH₂CH(CH₃)CH₂CH(CH₃)₃ | CH₂CH₃ | H |
| I-114 | CH₂CH₂CH₂CH₃ | CH₂CH₃ | NH₂ |
| I-115 | CH₂CH₂CH₂CH₂CH₃ | CH₂CH₃ | NH₂ |
| I-116 | CH₂CH₂CH₂CH₂CH₃ | CH₂CH₃ | NH₂ |
| I-117 | CH₂CH(CH₃)CH₂CH₂CH₃ | CH₂CH₃ | NH₂ |
| I-118 | CH₂CH(CH₂CH₃)₂ | CH₂CH₃ | NH₂ |
| I-119 | CH₂CH₂CH₂CH₂CH₂CH₂CH₃ | CH₂CH₃ | NH₂ |
| I-120 | CH₂CH₂CH₂CH₂CH₂CH₂CH₂CH₃ | CH₂CH₃ | NH₂ |
| I-121 | CH₂CH₂CH₂CH₂CH₂CH₂CH₂CH₂CH₃ | CH₂CH₃ | NH₂ |
| I-122 | CH₂CH₂CH₂CH₂CH₂CH₂CH₂CH₂CH₂CH₃ | CH₂CH₃ | NH₂ |
| I-123 | CH₂CH₂CH(CH₃)CH₂CH(CH₃)₃ | CH₂CH₃ | NH₂ |
| I-124 | CH₂CH₂CH₂CH₃ | CH₂CH₃ | CH₃ |
| I-125 | CH₂CH₂CH₂CH₂CH₃ | CH₂CH₃ | CH₃ |
| I-126 | CH₂CH₂CH₂CH₂CH₂CH₃ | CH₂CH₃ | CH₃ |
| I-127 | CH₂CH(CH₃)CH₂CH₂CH₃ | CH₂CH₃ | CH₃ |
| I-128 | CH₂CH(CH₂CH₃)₂ | CH₂CH₃ | CH₃ |
| I-129 | CH₂CH₂CH₂CH₂CH₂CH₂CH₃ | CH₂CH₃ | CH₃ |
| I-130 | CH₂CH₂CH₂CH₂CH₂CH₂CH₂CH₃ | CH₂CH₃ | CH₃ |
| I-131 | CH₂CH₂CH₂CH₂CH₂CH₂CH₂CH₂CH₃ | CH₂CH₃ | CH₃ |
| I-132 | CH₂CH₂CH₂CH₂CH₂CH₂CH₂CH₂CH₂CH₃ | CH₂CH₃ | CH₃ |
| I-133 | CH₂CH₂CH(CH₃)CH₂CH(CH₃)₃ | CH₂CH₃ | CH₃ |
| I-134 | (CH₂)₃—O—CH₃ | CH₂CH₃ | H |
| I-135 | (CH₂)₃—O—CH₂CH₃ | CH₂CH₃ | H |
| I-136 | (CH₂)₃—O—CH₂CH₂CH₃ | CH₂CH₃ | H |
| I-137 | (CH₂)₃—O—CH₂CH₂CH₂CH₃ | CH₂CH₃ | H |
| I-138 | (CH₂)₃—O—CH₂CH₂CH₂CH₂CH₃ | CH₂CH₃ | H |
| I-139 | (CH₂)₃—O—CH₂CH₂CH₂CH₂CH₂CH₃ | CH₂CH₃ | H |
| I-140 | (CH₂)₃—O—CH₂CH₂CH₂CH₂CH₂CH₂CH₃ | CH₂CH₃ | H |
| I-141 | (CH₂)₃—O—CH₂CH₂CH₂CH₂CH₂CH₂CH₂CH₃ | CH₂CH₃ | H |
| I-142 | (CH₂)₃—O—CH₂CH₂CH₂CH₂CH₂CH₂CH₂CH₂CH₃ | CH₂CH₃ | H |
| I-143 | (CH₂)₃—O—CH(CH₃)₂ | CH₂CH₃ | H |
| I-144 | (CH₂)₃—O—C(CH₃)₃ | CH₂CH₃ | H |
| I-145 | (CH₂)₃—O—CH₂C(CH₃)₃ | CH₂CH₃ | H |
| I-146 | (CH₂)₃—O—CH(CH₃)CH₂C(CH₃)₃ | CH₂CH₃ | H |
| I-147 | (CH₂)₃—O—CH(CH₂CH₃)CH₂C(CH₃)₃ | CH₂CH₃ | H |
| I-148 | (CH₂)₃—O—CH₂CH(CH₃)CH₂CH(CH₃)₂ | CH₂CH₃ | H |
| I-149 | (CH₂)₃—O—CH₂CH(CH₂CH₃)CH₂CH₂CH₃ | CH₂CH₃ | H |
| I-150 | (CH₂)₃—O—CH₂CH₂CH(CH₃)CH₂CH(CH₃)₂ | CH₂CH₃ | H |
| I-151 | (CH₂)₃—O—CH₂CH₂CH(CH₃)CH₂C(CH₃)₃ | CH₂CH₃ | H |
| I-152 | (CH₂)₃—O—CH₂CH₂CH(CH₃)CH₂CH₂CH(CH₃)₂ | CH₂CH₃ | H |
| I-153 | (CH₂)₃—O—CH₂CH₂CH(CH₃)CH₂CH₂CH₂CH(CH₃)₂ | CH₂CH₃ | H |
| I-154 | (CH₂)₃—O—CH₃ | CH₂CH₃ | CH₃ |
| I-155 | (CH₂)₃—O—CH₂CH₃ | CH₂CH₃ | CH₃ |
| I-156 | (CH₂)₃—O—CH₂CH₂CH₃ | CH₂CH₃ | CH₃ |

TABLE I-continued

| No. | R¹ | R² | R³ |
|---|---|---|---|
| I-157 | (CH$_2$)$_3$—O—CH$_2$CH$_2$CH$_3$ | CH$_2$CH$_3$ | CH$_3$ |
| I-158 | (CH$_2$)$_3$—O—CH$_2$CH$_2$CH$_2$CH$_3$ | CH$_2$CH$_3$ | CH$_3$ |
| I-159 | (CH$_2$)$_3$—O—CH$_2$CH$_2$CH$_2$CH$_2$CH$_3$ | CH$_2$CH$_3$ | CH$_3$ |
| I-160 | (CH$_2$)$_3$—O—CH$_2$CH$_2$CH$_2$CH$_2$CH$_2$CH$_3$ | CH$_2$CH$_3$ | CH$_3$ |
| I-161 | (CH$_2$)$_3$—O—CH$_2$CH$_2$CH$_2$CH$_2$CH$_2$CH$_2$CH$_3$ | CH$_2$CH$_3$ | CH$_3$ |
| I-162 | (CH$_2$)$_3$—O—CH$_2$CH$_2$CH$_2$CH$_2$CH$_2$CH$_2$CH$_2$CH$_3$ | CH$_2$CH$_3$ | CH$_3$ |
| I-163 | (CH$_2$)$_3$—O—CH(CH$_3$)$_2$ | CH$_2$CH$_3$ | CH$_3$ |
| I-164 | (CH$_2$)$_3$—O—C(CH$_3$)$_3$ | CH$_2$CH$_3$ | CH$_3$ |
| I-165 | (CH$_2$)$_3$—O—CH$_2$C(CH$_3$)$_3$ | CH$_2$CH$_3$ | CH$_3$ |
| I-166 | (CH$_2$)$_3$—O—CH(CH$_3$)CH$_2$C(CH$_3$)$_3$ | CH$_2$CH$_3$ | CH$_3$ |
| I-167 | (CH$_2$)$_3$—O—CH(CH$_2$CH$_3$)CH$_2$C(CH$_3$)$_3$ | CH$_2$CH$_3$ | CH$_3$ |
| I-168 | (CH$_2$)$_3$—O—CH$_2$CH(CH$_3$)CH$_2$CH(CH$_3$)$_2$ | CH$_2$CH$_3$ | CH$_3$ |
| I-169 | (CH$_2$)$_3$—O—CH$_2$CH(CH$_2$CH$_3$)CH$_2$CH$_2$CH$_3$ | CH$_2$CH$_3$ | CH$_3$ |
| I-170 | (CH$_2$)$_3$—O—CH$_2$CH$_2$CH(CH$_3$)CH$_2$CH(CH$_3$)$_2$ | CH$_2$CH$_3$ | CH$_3$ |
| I-171 | (CH$_2$)$_3$—O—CH$_2$CH$_2$CH(CH$_3$)CH$_2$C(CH$_3$)$_3$ | CH$_2$CH$_3$ | CH$_3$ |
| I-172 | (CH$_2$)$_3$—O—CH$_2$CH$_2$CH(CH$_3$)CH$_2$CH$_2$CH(CH$_3$)$_2$ | CH$_2$CH$_3$ | CH$_3$ |
| I-173 | (CH$_2$)$_3$—O—CH$_2$CH$_2$CH(CH$_3$)CH$_2$CH$_2$CH$_2$CH(CH$_3$)$_2$ | CH$_2$CH$_3$ | CH$_3$ |
| I-174 | CH$_2$CH$_2$CH$_3$ | CH$_2$CH$_2$CH$_3$ | H |
| I-175 | CH$_2$CH$_2$CH$_2$CH$_3$ | CH$_2$CH$_2$CH$_3$ | H |
| I-176 | CH$_2$CH$_2$CH$_2$CH$_2$CH$_2$CH$_3$ | CH$_2$CH$_2$CH$_3$ | H |
| I-177 | CH$_2$CH(CH$_3$)CH$_2$CH$_2$CH$_3$ | CH$_2$CH$_2$CH$_3$ | H |
| I-178 | CH$_2$CH(CH$_2$CH$_3$)$_2$ | CH$_2$CH$_2$CH$_3$ | H |
| I-179 | CH$_2$CH$_2$CH$_2$CH$_2$CH$_2$CH$_2$CH$_3$ | CH$_2$CH$_2$CH$_3$ | H |
| I-180 | CH$_2$CH$_2$CH$_2$CH$_2$CH$_2$CH$_2$CH$_2$CH$_3$ | CH$_2$CH$_2$CH$_3$ | H |
| I-181 | CH$_2$CH$_2$CH$_2$CH$_2$CH$_2$CH$_2$CH$_2$CH$_2$CH$_3$ | CH$_2$CH$_2$CH$_3$ | H |
| I-182 | CH$_2$CH$_2$CH$_2$CH$_2$CH$_2$CH$_2$CH$_2$CH$_2$CH$_2$CH$_3$ | CH$_2$CH$_2$CH$_3$ | H |
| I-183 | CH$_2$CH$_2$CH(CH$_3$)CH$_2$CH(CH$_3$)$_3$ | CH$_2$CH$_2$CH$_3$ | H |
| I-184 | CH$_2$—O—CH$_2$CH$_2$CH$_3$ | CH$_2$CH$_2$CH$_3$ | H |
| I-185 | CH$_2$—O—CH$_2$CH$_2$CH$_2$CH$_3$ | CH$_2$CH$_2$CH$_3$ | H |
| I-186 | CH$_2$—O—CH$_2$CH$_2$CH$_2$CH$_2$CH$_3$ | CH$_2$CH$_2$CH$_3$ | H |
| I-187 | CH$_2$—O—CH$_2$CH$_2$CH$_2$CH$_2$CH$_2$CH$_3$ | CH$_2$CH$_2$CH$_3$ | H |
| I-188 | CH$_2$—O—CH$_2$CH$_2$CH$_2$CH$_2$CH$_2$CH$_2$CH$_3$ | CH$_2$CH$_2$CH$_3$ | H |
| I-189 | CH$_2$—O—CH$_2$CH$_2$CH$_2$CH$_2$CH$_2$CH$_2$CH$_2$CH$_2$CH$_3$ | CH$_2$CH$_2$CH$_3$ | H |
| I-190 | CH$_2$—O—C(CH$_3$)$_3$ | CH$_2$CH$_2$CH$_3$ | H |
| I-191 | CH$_2$—O—CH$_2$C(CH$_3$)$_3$ | CH$_2$CH$_2$CH$_3$ | H |
| I-192 | CH$_2$—O—CH(CH$_3$)CH$_2$C(CH$_3$)$_3$ | CH$_2$CH$_2$CH$_3$ | H |
| I-193 | CH$_2$—O—CH(CH$_2$CH$_3$)CH$_2$C(CH$_3$)$_3$ | CH$_2$CH$_2$CH$_3$ | H |
| I-194 | CH$_2$—O—CH$_2$CH(CH$_3$)CH$_2$CH(CH$_3$)$_2$ | CH$_2$CH$_2$CH$_3$ | H |
| I-195 | CH$_2$—O—CH$_2$CH(CH$_2$CH$_3$)CH$_2$CH$_2$CH$_3$ | CH$_2$CH$_2$CH$_3$ | H |
| I-196 | CH$_2$—O—CH$_2$CH$_2$CH(CH$_3$)CH$_2$CH(CH$_3$)$_2$ | CH$_2$CH$_2$CH$_3$ | H |
| I-197 | CH$_2$—O—CH$_2$CH$_2$CH(CH$_3$)CH$_2$C(CH$_3$)$_3$ | CH$_2$CH$_2$CH$_3$ | H |
| I-198 | CH$_2$—O—CH$_2$CH$_2$CH(CH$_3$)CH$_2$CH$_2$CH(CH$_3$)$_2$ | CH$_2$CH$_2$CH$_3$ | H |
| I-199 | CH$_2$—O—CH$_2$CH$_2$CH(CH$_3$)CH$_2$CH$_2$CH$_2$CH(CH$_3$)$_2$ | CH$_2$CH$_2$CH$_3$ | H |
| I-200 | (CH$_2$)$_2$—O—CH$_2$CH$_2$CH$_3$ | CH$_2$CH$_2$CH$_3$ | H |
| I-201 | (CH$_2$)$_2$—O—CH$_2$CH$_2$CH$_2$CH$_3$ | CH$_2$CH$_2$CH$_3$ | H |
| I-202 | (CH$_2$)$_2$—O—CH$_2$CH$_2$CH$_2$CH$_2$CH$_3$ | CH$_2$CH$_2$CH$_3$ | H |
| I-203 | (CH$_2$)$_2$—O—CH$_2$CH$_2$CH$_2$CH$_2$CH$_2$CH$_3$ | CH$_2$CH$_2$CH$_3$ | H |
| I-204 | (CH$_2$)$_2$—O—CH$_2$CH$_2$CH$_2$CH$_2$CH$_2$CH$_2$CH$_3$ | CH$_2$CH$_2$CH$_3$ | H |
| I-205 | (CH$_2$)$_2$—O—CH$_2$CH$_2$CH$_2$CH$_2$CH$_2$CH$_2$CH$_2$CH$_3$ | CH$_2$CH$_2$CH$_3$ | H |
| I-206 | (CH$_2$)$_2$—O—CH$_2$CH$_2$CH$_2$CH$_2$CH$_2$CH$_2$CH$_2$CH$_2$CH$_3$ | CH$_2$CH$_2$CH$_3$ | H |
| I-207 | (CH$_2$)$_2$—O—CH(CH$_3$)$_2$ | CH$_2$CH$_2$CH$_3$ | H |
| I-208 | (CH$_2$)$_2$—O—C(CH$_3$)$_3$ | CH$_2$CH$_2$CH$_3$ | H |
| I-209 | (CH$_2$)$_2$—O—CH$_2$C(CH$_3$)$_3$ | CH$_2$CH$_2$CH$_3$ | H |
| I-210 | (CH$_2$)$_2$—O—CH(CH$_3$)CH$_2$C(CH$_3$)$_3$ | CH$_2$CH$_2$CH$_3$ | H |
| I-211 | (CH$_2$)$_2$—O—CH(CH$_2$CH$_3$)CH$_2$C(CH$_3$)$_3$ | CH$_2$CH$_2$CH$_3$ | H |
| I-212 | (CH$_2$)$_2$—O—CH$_2$CH(CH$_3$)CH$_2$CH(CH$_3$)$_2$ | CH$_2$CH$_2$CH$_3$ | H |
| I-213 | (CH$_2$)$_2$—O—CH$_2$CH(CH$_2$CH$_3$)CH$_2$CH$_2$CH$_3$ | CH$_2$CH$_2$CH$_3$ | H |
| I-214 | (CH$_2$)$_2$—O—CH$_2$CH$_2$CH(CH$_3$)CH$_2$CH(CH$_3$)$_2$ | CH$_2$CH$_2$CH$_3$ | H |
| I-215 | (CH$_2$)$_2$—O—CH$_2$CH$_2$CH(CH$_3$)CH$_2$C(CH$_3$)$_3$ | CH$_2$CH$_2$CH$_3$ | H |
| I-216 | (CH$_2$)$_2$—O—CH$_2$CH$_2$CH(CH$_3$)CH$_2$CH$_2$CH(CH$_3$)$_2$ | CH$_2$CH$_2$CH$_3$ | H |
| I-217 | (CH$_2$)$_2$—O—CH$_2$CH$_2$CH(CH$_3$)CH$_2$CH$_2$CH$_2$CH(CH$_3$)$_2$ | CH$_2$CH$_2$CH$_3$ | H |
| I-218 | (CH$_2$)$_3$—O—CH$_3$ | CH$_2$CH$_2$CH$_3$ | H |
| I-219 | (CH$_2$)$_3$—O—CH$_2$CH$_3$ | CH$_2$CH$_2$CH$_3$ | H |
| I-220 | (CH$_2$)$_3$—O—CH$_2$CH$_2$CH$_3$ | CH$_2$CH$_2$CH$_3$ | H |
| I-221 | (CH$_2$)$_3$—O—CH$_2$CH$_2$CH$_3$ | CH$_2$CH$_2$CH$_3$ | H |
| I-222 | (CH$_2$)$_3$—O—CH$_2$CH$_2$CH$_2$CH$_3$ | CH$_2$CH$_2$CH$_3$ | H |
| I-223 | (CH$_2$)$_3$—O—CH$_2$CH$_2$CH$_2$CH$_2$CH$_3$ | CH$_2$CH$_2$CH$_3$ | H |
| I-224 | (CH$_2$)$_3$—O—CH$_2$CH$_2$CH$_2$CH$_2$CH$_2$CH$_3$ | CH$_2$CH$_2$CH$_3$ | H |
| I-225 | (CH$_2$)$_3$—O—CH$_2$CH$_2$CH$_2$CH$_2$CH$_2$CH$_2$CH$_3$ | CH$_2$CH$_2$CH$_3$ | H |
| I-226 | (CH$_2$)$_3$—O—CH$_2$CH$_2$CH$_2$CH$_2$CH$_2$CH$_2$CH$_2$CH$_3$ | CH$_2$CH$_2$CH$_3$ | H |
| I-227 | (CH$_2$)$_3$—O—CH(CH$_3$)$_2$ | CH$_2$CH$_2$CH$_3$ | H |
| I-228 | (CH$_2$)$_3$—O—C(CH$_3$)$_3$ | CH$_2$CH$_2$CH$_3$ | H |
| I-229 | (CH$_2$)$_3$—O—CH$_2$C(CH$_3$)$_3$ | CH$_2$CH$_2$CH$_3$ | H |
| I-230 | (CH$_2$)$_3$—O—CH(CH$_3$)CH$_2$C(CH$_3$)$_3$ | CH$_2$CH$_2$CH$_3$ | H |
| I-231 | (CH$_2$)$_3$—O—CH(CH$_2$CH$_3$)CH$_2$C(CH$_3$)$_3$ | CH$_2$CH$_2$CH$_3$ | H |
| I-232 | (CH$_2$)$_3$—O—CH$_2$CH(CH$_3$)CH$_2$CH(CH$_3$)$_2$ | CH$_2$CH$_2$CH$_3$ | H |
| I-233 | (CH$_2$)$_3$—O—CH$_2$CH(CH$_2$CH$_3$)CH$_2$CH$_2$CH$_3$ | CH$_2$CH$_2$CH$_3$ | H |
| I-234 | (CH$_2$)$_3$—O—CH$_2$CH$_2$CH(CH$_3$)CH$_2$CH(CH$_3$)$_2$ | CH$_2$CH$_2$CH$_3$ | H |

TABLE I-continued

| No. | R$^1$ | R$^2$ | R$^3$ |
|---|---|---|---|
| I-235 | (CH$_2$)$_3$—O—CH$_2$CH$_2$CH(CH$_3$)CH$_2$C(CH$_3$)$_3$ | CH$_2$CH$_2$CH$_3$ | H |
| I-236 | (CH$_2$)$_3$—O—CH$_2$CH$_2$CH(CH$_3$)CH$_2$CH$_2$CH(CH$_3$)$_2$ | CH$_2$CH$_2$CH$_3$ | H |
| I-237 | (CH$_2$)$_3$—O—CH$_2$CH$_2$CH(CH$_3$)CH$_2$CH$_2$CH$_2$CH(CH$_3$)$_2$ | CH$_2$CH$_2$CH$_3$ | H |
| I-238 | CH$_2$CH$_2$CH$_3$ | CH$_2$OCH$_3$ | H |
| I-239 | CH$_2$CH$_2$CH$_2$CH$_3$ | CH$_2$OCH$_3$ | H |
| I-240 | CH$_2$CH$_2$CH$_2$CH$_2$CH$_3$ | CH$_2$OCH$_3$ | H |
| I-241 | CH$_2$CH$_2$CH$_2$CH$_2$CH$_2$CH$_3$ | CH$_2$OCH$_3$ | H |
| I-242 | CH$_2$CH(CH$_3$)CH$_2$CH$_2$CH$_3$ | CH$_2$OCH$_3$ | H |
| I-243 | CH$_2$CH(CH$_2$CH$_3$)$_2$ | CH$_2$OCH$_3$ | H |
| I-244 | CH$_2$CH$_2$CH$_2$CH$_2$CH$_2$CH$_2$CH$_3$ | CH$_2$OCH$_3$ | H |
| I-245 | CH$_2$CH$_2$CH$_2$CH$_2$CH$_2$CH$_2$CH$_2$CH$_3$ | CH$_2$OCH$_3$ | H |
| I-246 | CH$_2$CH$_2$CH$_2$CH$_2$CH$_2$CH$_2$CH$_2$CH$_2$CH$_3$ | CH$_2$OCH$_3$ | H |
| I-247 | CH$_2$CH$_2$CH$_2$CH$_2$CH$_2$CH$_2$CH$_2$CH$_2$CH$_2$CH$_3$ | CH$_2$OCH$_3$ | H |
| I-248 | CH$_2$CH$_2$CH(CH$_3$)CH$_2$CH(CH$_3$)$_3$ | CH$_2$OCH$_3$ | H |
| I-249 | (CH$_2$)$_3$—O—CH$_3$ | CH$_2$OCH$_3$ | H |
| I-250 | (CH$_2$)$_3$—O—CH$_2$CH$_3$ | CH$_2$OCH$_3$ | H |
| I-251 | (CH$_2$)$_3$—O—CH$_2$CH$_2$CH$_3$ | CH$_2$OCH$_3$ | H |
| I-252 | (CH$_2$)$_3$—O—CH$_2$CH$_2$CH$_2$CH$_3$ | CH$_2$OCH$_3$ | H |
| I-253 | (CH$_2$)$_3$—O—CH$_2$CH$_2$CH$_2$CH$_2$CH$_3$ | CH$_2$OCH$_3$ | H |
| I-254 | (CH$_2$)$_3$—O—CH$_2$CH$_2$CH$_2$CH$_2$CH$_2$CH$_3$ | CH$_2$OCH$_3$ | H |
| I-255 | (CH$_2$)$_3$—O—CH$_2$CH$_2$CH$_2$CH$_2$CH$_2$CH$_2$CH$_3$ | CH$_2$OCH$_3$ | H |
| I-256 | (CH$_2$)$_3$—O—CH$_2$CH$_2$CH$_2$CH$_2$CH$_2$CH$_2$CH$_2$CH$_3$ | CH$_2$OCH$_3$ | H |
| I-257 | (CH$_2$)$_3$—O—CH$_2$CH$_2$CH$_2$CH$_2$CH$_2$CH$_2$CH$_2$CH$_2$CH$_3$ | CH$_2$OCH$_3$ | H |
| I-258 | (CH$_2$)$_3$—O—CH(CH$_3$)$_2$ | CH$_2$OCH$_3$ | H |
| I-259 | (CH$_2$)$_3$—O—C(CH$_3$)$_3$ | CH$_2$OCH$_3$ | H |
| I-260 | (CH$_2$)$_3$—O—CH$_2$C(CH$_3$)$_3$ | CH$_2$OCH$_3$ | H |
| I-261 | (CH$_2$)$_3$—O—CH(CH$_3$)CH$_2$C(CH$_3$)$_3$ | CH$_2$OCH$_3$ | H |
| I-262 | (CH$_2$)$_3$—O—CH(CH$_2$CH$_3$)CH$_2$C(CH$_3$)$_3$ | CH$_2$OCH$_3$ | H |
| I-263 | (CH$_2$)$_3$—O—CH$_2$CH(CH$_3$)CH$_2$CH(CH$_3$)$_2$ | CH$_2$OCH$_3$ | H |
| I-264 | (CH$_2$)$_3$—O—CH$_2$CH(CH$_2$CH$_3$)CH$_2$CH$_2$CH$_3$ | CH$_2$OCH$_3$ | H |
| I-265 | (CH$_2$)$_3$—O—CH$_2$CH$_2$CH(CH$_3$)CH$_2$CH(CH$_3$)$_2$ | CH$_2$OCH$_3$ | H |
| I-266 | (CH$_2$)$_3$—O—CH$_2$CH$_2$CH(CH$_3$)CH$_2$C(CH$_3$)$_3$ | CH$_2$OCH$_3$ | H |
| I-267 | (CH$_2$)$_3$—O—CH$_2$CH$_2$CH(CH$_3$)CH$_2$CH$_2$CH(CH$_3$)$_2$ | CH$_2$OCH$_3$ | H |
| I-268 | (CH$_2$)$_3$—O—CH$_2$CH$_2$CH(CH$_3$)CH$_2$CH$_2$CH$_2$CH(CH$_3$)$_2$ | CH$_2$OCH$_3$ | H |
| I-269 | CH$_3$ | (CH$_2$)$_3$CH$_3$ | H |
| I-270 | CH$_2$CH$_3$ | (CH$_2$)$_3$CH$_3$ | H |
| I-271 | CH$_2$CH$_2$CH$_3$ | (CH$_2$)$_3$CH$_3$ | H |
| I-272 | CH$_2$CH$_2$CH$_2$CH$_3$ | (CH$_2$)$_3$CH$_3$ | H |
| I-273 | CH$_2$CH$_2$CH$_2$CH$_2$CH$_3$ | (CH$_2$)$_3$CH$_3$ | H |
| I-274 | CH$_3$ | (CH$_2$)$_4$CH$_3$ | H |
| I-275 | CH$_2$CH$_3$ | (CH$_2$)$_4$CH$_3$ | H |
| I-276 | CH$_2$CH$_2$CH$_3$ | (CH$_2$)$_4$CH$_3$ | H |
| I-277 | CH$_2$CH$_2$CH$_2$CH$_3$ | (CH$_2$)$_4$CH$_3$ | H |
| I-278 | CH$_2$CH$_2$CH$_2$CH$_2$CH$_3$ | (CH$_2$)$_4$CH$_3$ | H |
| I-279 | CH$_3$ | (CH$_2$)$_5$CH$_3$ | H |
| I-280 | CH$_2$CH$_3$ | (CH$_2$)$_5$CH$_3$ | H |
| I-281 | CH$_2$CH$_2$CH$_3$ | (CH$_2$)$_5$CH$_3$ | H |
| I-282 | CH$_2$CH$_2$CH$_2$CH$_3$ | (CH$_2$)$_5$CH$_3$ | H |
| I-283 | CH$_2$CH$_2$CH$_2$CH$_2$CH$_3$ | (CH$_2$)$_5$CH$_3$ | H |
| I-284 | CH$_3$ | (CH$_2$)$_6$CH$_3$ | H |
| I-285 | CH$_2$CH$_3$ | (CH$_2$)$_6$CH$_3$ | H |
| I-286 | CH$_2$CH$_2$CH$_3$ | (CH$_2$)$_6$CH$_3$ | H |
| I-287 | CH$_2$CH$_2$CH$_2$CH$_3$ | (CH$_2$)$_6$CH$_3$ | H |
| I-288 | CH$_2$CH$_2$CH$_2$CH$_2$CH$_3$ | (CH$_2$)$_6$CH$_3$ | H |
| I-289 | CH$_3$ | (CH$_2$)$_7$CH$_3$ | H |
| I-290 | CH$_2$CH$_3$ | (CH$_2$)$_7$CH$_3$ | H |
| I-291 | CH$_2$CH$_2$CH$_3$ | (CH$_2$)$_7$CH$_3$ | H |
| I-292 | CH$_2$CH$_2$CH$_2$CH$_3$ | (CH$_2$)$_7$CH$_3$ | H |
| I-293 | CH$_2$CH$_2$CH$_2$CH$_2$CH$_3$ | (CH$_2$)$_7$CH$_3$ | H |
| I-294 | CH$_3$ | (CH$_2$)$_8$CH$_3$ | H |
| I-295 | CH$_2$CH$_3$ | (CH$_2$)$_8$CH$_3$ | H |
| I-296 | CH$_2$CH$_2$CH$_3$ | (CH$_2$)$_8$CH$_3$ | H |
| I-297 | CH$_2$CH$_2$CH$_2$CH$_3$ | (CH$_2$)$_8$CH$_3$ | H |
| I-298 | CH$_2$CH$_2$CH$_2$CH$_2$CH$_3$ | (CH$_2$)$_8$CH$_3$ | H |

Preferred embodiments of the mixtures according to the invention comprise, as active component 1, a compound selected from the following list:
6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 5-ethyl-6-octyl-[1,2,4]triazolo[1,5-a]pyrimidine-2,7-diamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine and
5-trifluoromethyl-6-(3,5,5-trimethylhexyl)-[1,2,4]triazolo[1,5-a]pyrimidin-7-ylamine.

Further preferred embodiments of the mixtures according to the invention relate to combinations of one of the compounds of Table 1, in particular one of the preferred compounds I hereinabove, and one of the following active compounds II:

A) azoles, such as cyproconazole, difenoconazole, fluquinconazole, flusilazole, metconazole, propiconazole, prothioconazole, tebuconazole prochloraz, cyazofamid; carbendazim;
ethaboxam;

B) strobilurins, such as azoxystrobin, enestroburin, fluoxastrobin, pyraclostrobin, trifloxystrobin or methyl (2-chloro-5-[1-(3-methylbenzyloxyimino)-ethyl]benzyl)carbamate [B-6], methyl (2-chloro-5-[1-(6-methylpyridin-2-yl-methoxyimino)ethyl]benzyl)carbamate [B-7];

C) carboxamides, such as benalaxyl, boscalid, metalaxyl, ofurace, oxadixyl,
dimethomorph;
fluopicolide (picobenzamid), zoxamide;
mandipropamid;

D) heterocylic compounds, such as fluazinam;
cyprodinil, pyrimethanil;
dodemorph,
iprodione, vinclozolin;
famoxadone, fenamidone;
amisulbrom;
5-chloro-7-(4-methylpiperidin-1-yl)-6-(2,4,6-trifluorophenyl)-[1,2,4]triazolo[1,5-a]pyrimidine [D-8],
captan, folpet;

E) carbamates, such as mancozeb, maneb, metiram, propineb;
iprovalicarb, flubenthiavalicarb;
methyl 3-(4-chlorophenyl)-3-(2-isopropoxycarbonylamino-3-methyl-butyrylamino)propanoate [E-7];
and F) other active compounds, selected from
sulfur-containing heterocyclyl compounds: dithianon;
organophosphorus compounds: fosetyl, fosetyl-aluminum, phosphorous acid and its salts;
organochlorine compounds: chlorothalonil, thiophanate-methyl;
inorganic active compounds: Bordeaux mixture, copper acetate, copper hydroxide, copper oxychloride, basic copper sulfate;
others: cymoxanil, metrafenone;
growth retardants: prohexadione and its salts.

Preferred embodiments relate to the compositions listed in table A, where in each case one row of table A corresponds to a fungicidal composition comprising the particular compound of the formula I mentioned (component 1) and one active compound of the groups mentioned, this active compound preferably being selected from the preferred embodiments defined above.

TABLE A

| Row | Component 1 | Component 2 |
| --- | --- | --- |
| A-1 | Tab. 1, I-9 | an active compound II from group A |
| A-2 | Tab. 1, I-9 | an active compound II from group B |
| A-3 | Tab. 1, I-9 | an active compound II from group C |
| A-4 | Tab. 1, I-9 | an active compound II from group D |
| A-5 | Tab. 1, I-9 | an active compound II from group E |
| A-6 | Tab. 1, I-9 | an active compound II from group F |
| A-7 | Tab. 1, I-18 | an active compound II from group A |
| A-8 | Tab. 1, I-18 | an active compound II from group B |
| A-9 | Tab. 1, I-18 | an active compound II from group C |
| A-10 | Tab. 1, I-18 | an active compound II from group D |
| A-11 | Tab. 1, I-18 | an active compound II from group E |
| A-12 | Tab. 1, I-18 | an active compound II from group F |
| A-13 | Tab. 1, I-25 | an active compound II from group A |
| A-14 | Tab. 1, I-25 | an active compound II from group B |
| A-15 | Tab. 1, I-25 | an active compound II from group C |
| A-16 | Tab. 1, I-25 | an active compound II from group D |
| A-17 | Tab. 1, I-25 | an active compound II from group E |
| A-18 | Tab. 1, I-25 | an active compound II from group F |
| A-19 | Tab. 1, I-28 | an active compound II from group A |
| A-20 | Tab. 1, I-28 | an active compound II from group B |
| A-21 | Tab. 1, I-28 | an active compound II from group C |
| A-22 | Tab. 1, I-28 | an active compound II from group D |
| A-23 | Tab. 1, I-28 | an active compound II from group E |
| A-24 | Tab. 1, I-28 | an active compound II from group F |
| A-25 | Tab. 1, I-98 | an active compound II from group A |
| A-26 | Tab. 1, I-98 | an active compound II from group B |
| A-27 | Tab. 1, I-98 | an active compound II from group C |
| A-28 | Tab. 1, I-98 | an active compound II from group D |
| A-29 | Tab. 1, I-98 | an active compound II from group E |
| A-30 | Tab. 1, I-98 | an active compound II from group F |
| A-31 | Tab. 1, I-101 | an active compound II from group A |
| A-32 | Tab. 1, I-101 | an active compound II from group B |
| A-33 | Tab. 1, I-101 | an active compound II from group C |
| A-34 | Tab. 1, I-101 | an active compound II from group D |
| A-35 | Tab. 1, I-101 | an active compound II from group E |
| A-36 | Tab. 1, I-101 | an active compound II from group F |
| A-37 | Tab. 1, I-110 | an active compound II from group A |
| A-38 | Tab. 1, I-110 | an active compound II from group B |
| A-39 | Tab. 1, I-110 | an active compound II from group C |
| A-40 | Tab. 1, I-110 | an active compound II from group D |
| A-41 | Tab. 1, I-110 | an active compound II from group E |
| A-42 | Tab. 1, I-110 | an active compound II from group F |
| A-43 | Tab. 1, I-113 | an active compound II from group A |
| A-44 | Tab. 1, I-113 | an active compound II from group B |
| A-45 | Tab. 1, I-113 | an active compound II from group C |
| A-46 | Tab. 1, I-113 | an active compound II from group D |
| A-47 | Tab. 1, I-113 | an active compound II from group E |
| A-48 | Tab. 1, I-113 | an active compound II from group F |
| A-49 | Tab. 1, I-120 | an active compound II from group A |
| A-50 | Tab. 1, I-120 | an active compound II from group B |
| A-51 | Tab. 1, I-120 | an active compound II from group C |
| A-52 | Tab. 1, I-120 | an active compound II from group D |
| A-53 | Tab. 1, I-120 | an active compound II from group E |
| A-54 | Tab. 1, I-120 | an active compound II from group F |
| A-55 | Tab. 1, I-180 | an active compound II from group A |
| A-56 | Tab. 1, I-180 | an active compound II from group B |
| A-57 | Tab. 1, I-180 | an active compound II from group C |
| A-58 | Tab. 1, I-180 | an active compound II from group D |
| A-59 | Tab. 1, I-180 | an active compound II from group E |
| A-60 | Tab. 1, I-180 | an active compound II from group F |
| A-61 | Tab. 1, I-245 | an active compound II from group A |
| A-62 | Tab. 1, I-245 | an active compound II from group B |
| A-63 | Tab. 1, I-245 | an active compound II from group C |
| A-64 | Tab. 1, I-245 | an active compound II from group D |
| A-65 | Tab. 1, I-245 | an active compound II from group E |
| A-66 | Tab. 1, I-245 | an active compound II from group F |
| A-67 | Tab. 1, I-290 | an active compound II from group A |
| A-68 | Tab. 1, I-290 | an active compound II from group B |
| A-69 | Tab. 1, I-290 | an active compound II from group C |
| A-70 | Tab. 1, I-290 | an active compound II from group D |
| A-71 | Tab. 1, I-290 | an active compound II from group E |
| A-72 | Tab. 1, I-290 | an active compound II from group F |

The active compounds mentioned above can also be employed in the form of their agriculturally compatible salts. These are usually the alkali metal or alkaline earth metal salts, such as sodium, potassium or calcium salts.

When preparing the mixtures, preference is given to using the pure active compounds which, if required, may be mixed with further active compounds against harmful fungi or other pests, such as insects, arachnids or nematodes, or else herbicidal or growth-regulating active compounds or fertilizers as further active components.

In a preferred embodiment of the invention, mixtures of an azolopyrimidinylamine and an active compound II are used.

Under certain conditions, it may be advantageous to combine an azolopyrimidinylamine with two or more active compounds II. In addition, mixtures of two or more compounds I with one or more active compounds II may also be suitable.

Suitable further active components in the above sense are in particular the active compounds II, mentioned at the outset, and in particular the preferred active compounds mentioned above. In the case of ternary mixtures, preferred third active components are strobilurins, in particular pyraclostrobin, carboxamides, in particular boscalid, and also organophosphorus compounds, in particular phosphorous acid and its salts.

The compounds I and active compounds II are usually employed in a weight ratio of from 100:1 to 1:100, preferably from 50:1 to 1:50, preferably from 20:1 to 1:20, in particular from 10:1 to 1:10.

The further active components are, if desired, added in a ratio of from 50:1 to 1:50, preferably from 20:1 to 1:20, to the compound I.

Depending on the type of compound and the desired effect, the application rates of the mixtures according to the invention are from 5 g/ha to 2000 g/ha, preferably from 50 to 900 g/ha, in particular from 50 to 750 g/ha.

Correspondingly, the application rates for compounds I are generally from 1 to 1000 g/ha, preferably from 10 to 900 g/ha, in particular from 20 to 750 g/ha.

Depending on the type of active compound II, the application rates for active compounds II are generally from 1 to 2000 g/ha, preferably from 10 to 900 g/ha, in particular from 40 to 500 g/ha.

In the treatment of seed, for example by dusting, coating or soaking seeds, application rates of mixture are generally from 1 to 1000 g/100 kg of seed, preferably from 1 to 750 g/100 kg, in particular from 5 to 500 g/100 kg.

The method for controlling harmful fungi is carried out by the separate or joint application of the compounds I and active compounds II or the mixtures of compounds I and active compounds II by spraying or dusting the seeds, the plants or the soils before or after sowing of the plants or before or after emergence of the plants.

The mixtures according to the invention, or the compounds I and active compounds II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:
water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used,
carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Formulations for the treatment of seed may additionally comprise binders and/or gelling agents and, if appropriate, colorants.

In general, the formulations comprise from 0.01 to 95% by weight, preferably from 0.1 to 90% by weight, of the active compounds. The active compounds are employed in a purity of from 90% to 100%, preferably 95% to 100%.

For the treatment of seed, the formulations in question give, after two-to-tenfold dilution, active compound concentrations of from 0.01 to 60% by weight, preferably from 0.1 to 40% by weight, in the ready-to-use preparations.

The following are examples of formulations according to the invention:

1. Products for Dilution with Water

A Water-Soluble Concentrates (SL, LS)

10 parts by weight of a mixture according to the invention are dissolved in 90 parts by weight of water or in a water-soluble solvent. As an alternative, wetters or other auxiliaries are added. The active compound dissolves upon dilution with water. In this way, a formulation having a content of 10% by weight of active compound is obtained.

B Dispersible Concentrates (DC)

20 parts by weight of a mixture according to the invention are dissolved in 70 parts by weight of cyclohexanone with addition of 10 parts by weight of a dispersant, for example polyvinylpyrrolidone. Dilution with water gives a dispersion. The active compound content is 20% by weight C Emulsifiable Concentrates (EC)

15 parts by weight of a mixture according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of a mixture according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of a mixture according to the invention are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of a mixture according to the invention are ground finely with addition of 50 parts by weight of dispersants and wetters and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of a mixture according to the invention are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of a mixture according to the invention, 10 parts by weight of dispersant, 1 part by weight of gelling agent and 70 parts by weight of water or an organic solvent are ground to give a fine suspension. On dilution with water, a stable suspension having an active compound content of 20% by weight is obtained.

2. Products to be Applied Undiluted

I Dustable Powders (DP, DS)

5 parts by weight of a mixture according to the invention are ground finely and mixed intimately with 95 parts by weight of finely divided kaolin. This gives a dustable product having an active compound content of 5% by weight.

J Granules (GR, FG, GG, MG)

0.5 part by weight of a mixture according to the invention is ground finely and associated with 99.5 parts by weight of carriers. Current methods are extrusion, spray-drying or the fluidized bed. This gives granules to be applied undiluted having an active compound content of 0.5% by weight.

K ULV Solutions (UL)

10 parts by weight of a mixture according to the invention are dissolved in 90 parts by weight of an organic solvent, for example xylene. This gives a product to be applied undiluted having an active compound content of 10% by weight.

For seed treatment, use is usually made of water-soluble concentrates (LS), suspensions (FS), dustable powders (DS), water-dispersible and water-soluble powders (WS, SS), emulsions (ES), emulsifiable concentrates (EC) and gel formulations (GF). These formulations can be applied to the seed in undiluted form or, preferably, diluted. Application can be carried out prior to sowing.

Preference is given to using FS formulations for seed treatment. Usually, such formulations comprise from 1 to 800 g of active compound/l, from 1 to 200 g of surfactants/l, from 0 to 200 g of antifreeze agents/l, from 0 to 400 g of binder/l, from 0 to 200 g of colorants/l and solvents, preferably water.

Analogous formulations A to K of the compounds I or an active compound II comprise the respective amount of the individual active compounds. They are usually mixed directly prior to application during dilution to the ready-to-use active compound concentration (tank mix).

The active compound concentrations in the ready-to-use preparations may be varied within relatively wide ranges. In general, they are between 0.0001 and 10%, preferably between 0.01 and 1%.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (wettable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compounds may also be used successfully in the ultra-low-volume process (ULV), it being possible to apply formulations comprising over 95% by weight of active compound, or even to apply the active compound without additives.

Oils of various types, wetters, adjuvants, herbicides, fungicides, other pesticides, or bactericides may be added to the active compounds, even, if appropriate, not until immediately prior to use (tank mix). These agents may be admixed with the compositions according to the invention in a weight ratio of from 1:100 to 100:1, preferably from 1:10 to 10:1.

Suitable adjuvants in this sense are in particular: organically modified polysilo-xanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be carried out before or after infection by the harmful fungi.

USE EXAMPLES

The fungicidal effect of the compounds and the mixtures was demonstrated by the following tests:

The active compounds amisulbrom, Cu hydroxide, famoxadone, phosphorous acid and zoxamide were used as commercial formulations and diluted with water to the stated concentrations.

The active compounds were separately or jointly prepared as a stock solution comprising 25 mg of active compound which was made up to 10 ml using a mixture of acetone and/or DMSO and the emulsifier Uniperol® EL (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compound stated below.

Use Example 1

Persistency Against Late Blight on Tomatoes Caused by *Phytophthora infestans*

Leaves of potted plants of the cultivar "Great beef tomato St. Pierre" were sprayed to runoff point with an aqueous suspension having the concentration of active compound stated below. After 5 days, the leaves were inoculated with an aqueous spore suspension of *Phytophthora infestans*. The plants were then placed in a water vapor-saturated chamber at temperatures between 18 and 20° C. After 6 days, the late blight on the untreated but infected control plants had developed to such an extent that the infection could be determined visually in %.

The visually determined percentages of infected leaf areas were converted into efficacies in % of the untreated control:

The efficacy (E) is calculated as follows using Abbot's formula:

$$E = (1 - \alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, 20-22, 1967) and compared with the observed efficacies.

Colby's formula:

$$E = x + y - x \cdot y/100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b

TABLE A

Individual active compounds

| No. | Active compound | Concentration of active compound in the spray liquor [ppm] | Efficacy in % of the untreated control |
|---|---|---|---|
| 1 | control (untreated) | — | (90% infection) |
| 2 | Table 1; I-18 | 16 | 11 |
| 3 | Table 1; I-25 | 16 | 0 |
| 4 | Table 1; I-28 | 63 | 44 |
| 5 | Table 1; I-113 | 16 | 22 |
| 6 | Table 1; I-120 | 16 | 33 |
| 7 | Table 1; I-180 | 63 | 33 |
|   |   | 16 | 0 |
| 8 | Table 1; I-245 | 4 | 0 |
| 9 | metiram | 63 | 33 |
|   |   | 16 | 0 |
| 10 | cyazofamid | 4 | 33 |
| 11 | metalaxyl | 63 | 56 |
|   |   | 16 | 33 |
| 12 | dimethomorph | 4 | 33 |

TABLE B

Mixtures according to the invention of the active compounds from Table 1

| No. | Mixture of active compounds Concentration Mixing ratio | Observed efficacy | Calculated efficacy*) |
|---|---|---|---|
| 13 | I-18 + cyazofamid<br>16 + 4 ppm<br>4:1 | 97 | 41 |
| 14 | I-18 + dimethomorph<br>16 + 4 ppm<br>4:1 | 89 | 41 |
| 15 | I-25 + metiram<br>63 + 16 ppm<br>4:1 | 67 | 33 |
| 16 | I-25 + metalaxyl<br>16 + 63 ppm<br>1:4 | 83 | 56 |
| 17 | I-28 + metiram<br>63 + 16 ppm<br>4:1 | 89 | 44 |
| 18 | I-28 + metalaxyl<br>63 + 16 ppm<br>4:1 | 83 | 63 |
| 19 | I-113 + metiram<br>16 + 63 ppm<br>1:4 | 67 | 48 |
| 20 | I-113 + cyazofamid<br>16 + 4 ppm<br>4:1 | 67 | 48 |
| 21 | I-113 + metalaxyl<br>16 + 63 ppm<br>1:4 | 83 | 65 |
| 22 | I-113 + dimethomorph<br>16 + 4 ppm<br>4:1 | 67 | 48 |
| 23 | I-120 + cyazofamid<br>16 + 4 ppm<br>4:1 | 99 | 56 |
| 24 | I-120 + metalaxyl<br>16 + 63 ppm<br>1:4 | 94 | 70 |
| 25 | I-180 + metiram<br>16 + 63 ppm<br>1:4 | 89 | 33 |
| 26 | I-180 + metiram<br>63 + 63 ppm<br>1:1 | 99 | 56 |
| 27 | I-180 + cyazofamid<br>4 + 4 ppm<br>1:1 | 72 | 33 |

TABLE B-continued

Mixtures according to the invention of the active compounds from Table 1

| No. | Mixture of active compounds Concentration Mixing ratio | Observed efficacy | Calculated efficacy* |
|---|---|---|---|
| 28 | I-180 + cyazofamid 16 + 4 ppm 4:1 | 97 | 33 |
| 29 | I-180 + metalaxyl 16 + 63 ppm 1:4 | 94 | 56 |
| 30 | I-180 + dimethomorph 4 + 4 ppm 1:1 | 83 | 33 |
| 31 | I-180 + dimethomorph 16 + 4 ppm 4:1 | 97 | 33 |
| 32 | I-245 + metalaxyl 4 + 16 ppm 1:4 | 92 | 33 |

*)efficacy calculated using Colbys formula

Use Example 2

Activity Against Late Blight on Tomatoes Caused by *Phytophthora infestans*, Protective Treatment Leaves of potted tomato plants were sprayed to runoff point with an aqueous suspension having the active compound concentration stated below. After seven days, the leaves were infected with an aqueous sporangia suspension of *Phytophthora infestans*. The plants were then placed in a water vapor-saturated chamber at temperatures between 18 and 20° C. After 6 days, the late blight on the untreated but infected control plants had developed to such an extent that the infection could be determined visually in %.

Evaluation was carried out analogously to example 1.

| No. | Active compound/active compound combination | Conc. (mg/l) | Ratio | Observed activity (%) | Calculated activity according to Colby (%) |
|---|---|---|---|---|---|
| 33 | control | — | | 90% (infection) | |
| 34 | Tab. 1; I-110 [I-110] | 4 | | 11 | |
| 35 | Cu(OH)$_2$ | 63 | | 11 | |
| 36 | mancozeb | 63 | | 11 | |
| 37 | phosphorous acid disodium salt (Na$_2$HPO$_3$) | 63 | | 33 | |
| 38 | [I-110] + Cu(OH)$_2$ | 4 + 63 | 1:4 | 56 | 21 |
| 39 | [I-110] + mancozeb | 4 + 63 | 1:4 | 56 | 21 |
| 40 | [I-110] + Na$_2$HPO$_3$ | 4 + 63 | 1:16 | 67 | 41 |

Use Example 3

Activity Against *peronospora* of Grapevines Caused by *Plasmopara viticola*

Leaves of potted grapevines were sprayed to runoff point with an aqueous suspension having the active compound concentration stated below. After three days, the undersides of the leaves were inoculated with an aqueous sporangia suspension of *Plasmopara viticola*. The vines were then initially placed in a water vapor-saturated chamber at 24° C. for 24 hours and then in a greenhouse at temperatures between 20 and 30° C. for 5 days. After this time, the plants were again placed in a humid chamber for 16 hours to promote sporangiophore eruption. The extent of the development of the infection on the undersides of the leaves was then determined visually.

Evaluation was carried out analogously to example 1.

| No. | Active compound/active compound combination | Conc. (mg/l) | Ratio | Observed activity (%) | Calculated activity according to Colby (%) |
|---|---|---|---|---|---|
| 41 | control | | | 90% (infection) | |
| 42 | Tab. 1; I-110 [I-110] | 16 | | 56 | |
| | | 4 | | 0 | |
| | | 0.25 | | 0 | |
| 43 | [B-6] | 16 | | 0 | |
| 44 | amidosulbrom | 4 | | 22 | |
| 45 | famoxadone | 4 | | 0 | |
| 46 | iprovalicarb | 4 | | 0 | |
| 47 | [E-7] | 0.25 | | 0 | |
| 48 | zoxamide | 4 | | 11 | |
| 49 | ethaboxam | 0.25 | | 33 | |
| 50 | [I-110] + [B-6] | 16 + 16 | 1:1 | 78 | 56 |
| 51 | [I-110] + amidosulbrom | 4 + 4 | 1:1 | 94 | 22 |
| 52 | [I-110] + famoxadone | 4 + 4 | 1:1 | 78 | 0 |
| 53 | [I-110] + iprovalicarb | 4 + 4 | 1:1 | 44 | 0 |
| 54 | [I-110] + [E-7] | 0.25 + 0.25 | 1:1 | 56 | 0 |
| 55 | [I-110] + zoxamide | 4 + 4 | 1:1 | 56 | 11 |
| 56 | [I-110] + ethaboxam | 0.25 + 0.25 | 1:1 | 56 | 33 |

Use Example 4

Activity Against *peronospora* of Grapevines Caused by *Plasmopara viticola*

Leaves of potted grapevines were sprayed to runoff point with an aqueous suspension having the active compound concentration stated below. After seven days, the undersides of the leaves were inoculated with an aqueous sporangia suspension of *Plasmopara viticola*. The vines were then initially placed in a water vapor-saturated chamber at 24° C. for 24 hours and then in a greenhouse at temperatures between 20 and 30° C. for 5 days. After this time, the plants were again placed in a humid chamber for 16 hours to promote sporangiophore eruption. The extent of the development of the infection on the undersides of the leaves was then determined visually.

Evaluation was carried out analogously to example 1.

| No. | Active compound/active compound combination | Conc. (mg/l) | Ratio | Observed activity (%) | Calculated activity according to Colby (%) |
|---|---|---|---|---|---|
| 57 | control | | | 90% (infection) | |
| 58 | Tab. 1; I-110 [I-110] | 16 | | 0 | |
|    |                       | 4  | | 0 | |
| 59 | cymoxanil | 16 | | 33 | |
| 60 | dithianon | 16 | | 0 | |
| 61 | dimethomorph | 16 | | 67 | |
| 62 | [I-110] + cymoxanil | 16 + 16 | 1:1 | 56 | 33 |
| 63 | [I-110] + dithianon | 4 + 16 | 1:4 | 44 | 0 |
| 64 | [I-110] + dimethomorph | 4 + 16 | 1:4 | 97 | 67 |

Microtests

The active compounds were formulated separately as a stock solution of a concentration of 10 000 ppm in DMSO.

The active compounds fluazinam, pyraclostrobin, copper hydroxide, flubenthiavalicarb, phosphorous acid, dodemorph, zoxamide, amidosulbrom and trifloxystrobin were used as commercial formulations and diluted with water to the stated concentrations.

Use Example 5

Activity Against the Late Blight Pathogen *Phytophthora infestans* in the Microtiter Test The stock solution is pipetted onto a microtiter plate (MTP) and diluted to the stated active compound concentration using a pea juice-based aqueous nutrient medium for fungi. An aqueous zoospore suspension of *Phytophthora infestans* was then added. The plates were placed in a water vapor-saturated chamber at temperatures of 18° C. Using an absorption photometer, the MTPs were measured at 405 nm on day 7 after the inoculation.

The measured parameters were compared to the growth of the active compound-free control variant and the fungus- and active compound-free blank value to determine the relative growth in % of the pathogens in the individual active compounds.

| No. | Active compound/active compound combination | Conc. (mg/l) | Ratio | Observed activity (%) | Calculated activity according to Colby (%) |
|---|---|---|---|---|---|
| 65 | Tab. 1; I-9 [I-9] | 0.25 | | 7 | |
|    |                    | 0.063 | | 6 | |
|    |                    | 0.016 | | 1 | |
| 66 | Tab. 1; I-18 [I-18] | 1 | | 45 | |
|    |                      | 0.25 | | 16 | |
|    |                      | 0.063 | | 6 | |
| 67 | Tab. 1; I-25 [I-25] | 1 | | 13 | |
|    |                      | 0.25 | | 5 | |
|    |                      | 0.063 | | 4 | |
| 68 | Tab. 1; I-28 [I-28] | 1 | | 24 | |
|    |                      | 0.25 | | 14 | |
|    |                      | 0.063 | | 0 | |
|    |                      | 0.016 | | 0 | |
| 69 | Tab. 1; I-98 [I-98] | 4 | | 22 | |
|    |                      | 1 | | 16 | |
|    |                      | 0.25 | | 6 | |
|    |                      | 0.063 | | 5 | |
| 70 | Tab. 1; I-101 [I-101] | 4 | | 9 | |
|    |                        | 0.25 | | 3 | |
| 71 | Tab. 1; I-110 [I-110] | 1 | | 59 | |
|    |                        | 0.25 | | 5 | |
|    |                        | 0.063 | | 3 | |
|    |                        | 0.016 | | 1 | |
| 72 | Tab. 1; I-113 [I-113] | 4 | | 36 | |
|    |                        | 0.25 | | 3 | |
| 73 | Tab. 1; I-120 [I-120] | 0.25 | | 6 | |
|    |                        | 0.063 | | 2 | |
|    |                        | 0.016 | | 0 | |

-continued

| No. | Active compound/active compound combination | Conc. (mg/l) | Ratio | Observed activity (%) | Calculated activity according to Colby (%) |
|---|---|---|---|---|---|
| 74 | Tab. 1; I-180 [I-180] | 1 | | 17 | |
| | | 0.25 | | 8 | |
| | | 0.063 | | 2 | |
| | | 0.016 | | 0 | |
| 75 | Tab. 1; I-245 [I-245] | 0.25 | | 12 | |
| | | 0.063 | | 0 | |
| | | 0.016 | | 0 | |
| 76 | Tab. 1; I-290 [I-290] | 4 | | 3 | |
| | | 0.25 | | 0 | |
| | | 0.063 | | 0 | |
| 77 | fosetyl-Al | 4 | | 6 | |
| 78 | Cu(OH)$_2$ | 4 | | 2 | |
| 79 | folpet | 1 | | 6 | |
| 80 | captan | 1 | | 12 | |
| 81 | maneb | 1 | | 6 | |
| 82 | metiram | 16 | | 49 | |
| | | 4 | | 9 | |
| 83 | metalaxyl | 4 | | 9 | |
| | | 1 | | 6 | |
| 84 | flubenthiavalicarb | 0.25 | | 68 | |
| 85 | Na$_2$HPO$_3$ | 4 | | 6 | |
| 86 | Cu$_2$Cl(OH)$_3$ | 16 | | 18 | |
| 87 | cyprodinil | 4 | | 10 | |
| 88 | prochloraz | 16 | | 6 | |
| 89 | fenamidone | 0.063 | | 40 | |
| 90 | enestroburin | 1 | | 35 | |
| 91 | benalaxyl | 4 | | 13 | |
| 92 | oxadixyl | 16 | | 17 | |
| | | 4 | | 2 | |
| | | 1 | | 0 | |
| 93 | ofurace | 16 | | 19 | |
| | | 4 | | 0 | |
| 94 | difenoconazole | 4 | | 24 | |
| 95 | tebuconazole | 16 | | 9 | |
| | | 4 | | 10 | |
| | | 1 | | 8 | |
| 96 | propiconazole | 16 | | 12 | |
| | | 4 | | 11 | |
| | | 1 | | 1 | |
| 97 | cyproconazole | 4 | | 9 | |
| 98 | flusilazole | 4 | | 11 | |
| | | 1 | | 0 | |
| 99 | fluquinconazole | 4 | | 0 | |
| | | 1 | | 0 | |
| 100 | boscalid | 4 | | 17 | |
| | | 1 | | 2 | |
| 101 | metrafenone | 4 | | 2 | |
| 102 | [D-8] | 1 | | 43 | |
| 103 | vinclozolin | 16 | | 0 | |
| 104 | [B-6] | 0.25 | | 10 | |
| 105 | trifloxystrobin | 1 | | 46 | |
| | | 0.25 | | 33 | |
| 106 | fluazinam | 0.25 | | 9 | |
| 107 | mandipropamid | 0.25 | | 40 | |
| | | 0.063 | | 10 | |
| 108 | fluoxastrobin | 0.025 | | 2 | |
| | | 0.063 | | 1 | |
| 109 | azoxystrobin | 0.063 | | 21 | |
| 110 | pyraclostrobin | 0.063 | | 59 | |
| | | 0.016 | | 14 | |
| 111 | [I-9] + fenamidone | 0.016 + 0.063 | 1:4 | 63 | 41 |
| 112 | [I-9] + enestroburin | 0.25 + 1 | 1:4 | 92 | 40 |
| 113 | [I-9] + mandipropamid | 0.25 + 0.25 | 1:1 | 95 | 44 |
| 114 | [I-9] + fluoxastrobin | 0.25 + 0.25 | 1:1 | 91 | 9 |
| 115 | [I-9] + pyraclostrobin | 0.063 + 0.016 | 4:1 | 40 | 19 |
| 116 | [I-18] + cyprodinil | 1 + 4 | 1:4 | 83 | 59 |
| 117 | [I-18] + enestroburin | 0.25 + 1 | 1:4 | 91 | 45 |
| 118 | [I-18] + benalaxyl | 1 + 4 | 1:4 | 97 | 52 |
| 119 | [I-18] + oxadixyl | 1 + 4 | 1:4 | 96 | 46 |
| 120 | [I-18] + ofurace | 1 + 4 | 1:4 | 99 | 45 |
| 121 | [I-18] + difenoconazole | 1 + 4 | 1:4 | 89 | 58 |
| 122 | [I-18] + tebuconazole | 1 + 4 | 1:4 | 94 | 50 |
| 123 | [I-18] + propiconazole | 1 + 4 | 1:4 | 96 | 51 |
| 124 | [I-18] + mandipropamid | 0.25 + 0.25 | 1:1 | 96 | 50 |
| 125 | [I-18] + fluoxastrobin | 0.25 + 0.25 | 1:1 | 92 | 18 |

-continued

| No. | Active compound/active compound combination | Conc. (mg/l) | Ratio | Observed activity (%) | Calculated activity according to Colby (%) |
|---|---|---|---|---|---|
| 126 | [I-18] + azoxystrobin | 0.063 + 0.063 | 1:1 | 49 | 26 |
| 127 | [I-18] + pyraclostrobin | 0.063 + 0.016 | 4:1 | 39 | 19 |
| 128 | [I-25] + fosetyl-Al | 1 + 4 | 1:4 | 69 | 18 |
| 129 | [I-25] + Cu(OH)$_2$ | 1 + 4 | 1:4 | 95 | 15 |
| 130 | [I-25] + metiram | 1 + 4 | 1:4 | 98 | 21 |
| 131 | [I-25] + metalaxyl | 1 + 4 | 1:4 | 78 | 21 |
| 132 | [I-25] + Na$_2$HPO$_3$ | 1 + 4 | 1:4 | 74 | 15 |
| 133 | [I-25] + enestroburin | 0.25 + 1 | 1:4 | 94 | 38 |
| 134 | [I-25] + cyproconazole | 1 + 4 | 1:4 | 75 | 21 |
| 135 | [I-25] + flusilazole | 1 + 4 | 1:4 | 89 | 23 |
| 136 | [I-25] + fluquinconazole | 1 + 4 | 1:4 | 94 | 13 |
| 137 | [I-25] + boscalid | 1 + 4 | 1:4 | 95 | 28 |
| 138 | [I-25] + metrafenone | 1 + 4 | 1:4 | 90 | 14 |
| 139 | [I-25] + [B-6] | 0.25 + 0.25 | 1:1 | 58 | 15 |
| 140 | [I-25] + trifloxystrobin | 1 + 1 | 1:1 | 79 | 53 |
| 141 | [I-25] + pyraclostrobin | 0.063 + 0.016 | 4:1 | 95 | 17 |
| 142 | [I-28] + Cu(OH)$_2$ | 1 + 4 | 1:4 | 98 | 26 |
| 143 | [I-28] + flubenthiavalicarb | 0.063 + 0.25 | 1:4 | 99 | 68 |
| 144 | [I-28] + fenamidone | 0.016 + 0.063 | 1:4 | 63 | 40 |
| 145 | [I-28] + cyproconazole | 1 + 4 | 1:4 | 69 | 31 |
| 146 | [I-28] + flusilazole | 1 + 4 | 1:4 | 95 | 33 |
| 147 | [I-28] + fluquinconazole | 1 + 4 | 1:4 | 89 | 24 |
| 148 | [I-28] + boscalid | 1 + 4 | 1:4 | 89 | 37 |
| 149 | [I-28] + metrafenone | 1 + 4 | 1:4 | 78 | 26 |
| 150 | [I-28] + fluazinam | 0.25 + 0.25 | 1:1 | 67 | 22 |
| 151 | [I-28] + mandipropamid | 0.063 + 0.063 | 1:1 | 58 | 10 |
| 152 | [I-28] + fluoxastrobin | 0.25 + 0.25 | 1:1 | 95 | 16 |
| 153 | [I-28] + azoxystrobin | 0.063 + 0.063 | 1:1 | 77 | 21 |
| 154 | [I-28] + pyraclostrobin | 0.063 + 0.016 | 4:1 | 47 | 14 |
| 155 | [I-98] + Cu$_2$Cl(OH)$_3$ | 4 + 16 | 1:4 | 99 | 36 |
| 156 | [I-98] + enestroburin | 0.25 + 1 | 1:4 | 87 | 38 |
| 157 | [I-98] + tebuconazole | 4 + 16 | 1:4 | 69 | 29 |
| 158 | [I-98] + propiconazole | 4 + 16 | 1:4 | 83 | 31 |
| 159 | [I-98] + fluquinconazole | 1 + 4 | 1:4 | 65 | 16 |
| 160 | [I-98] + metrafenone | 1 + 4 | 1:4 | 47 | 17 |
| 161 | [I-98] + fluoxastrobin | 0.063 + 0.063 | 1:1 | 93 | 4 |
| 162 | [I-98] + azoxystrobin | 0.063 + 0.063 | 1:1 | 48 | 25 |
| 163 | [I-101] + maneb | 0.25 + 1 | 1:4 | 57 | 11 |
| 164 | [I-101] + Cu$_2$Cl(OH)$_3$ | 4 + 16 | 1:4 | 75 | 25 |
| 165 | [I-101] + prochloraz | 4 + 16 | 1:4 | 81 | 14 |
| 166 | [I-101] + enestroburin | 0.25 + 1 | 1:4 | 59 | 37 |
| 167 | [I-101] + vinclozolin | 4 + 16 | 1:4 | 48 | 9 |
| 168 | [I-101] + mandipropamid | 0.25 + 0.25 | 1:1 | 66 | 42 |
| 169 | [I-101] + fluoxastrobin | 0.25 + 0.25 | 1:1 | 91 | 5 |
| 170 | [I-101] + pyraclostrobin | 0.25 + 0.063 | 4:1 | 87 | 60 |
| 171 | [I-110] + metalaxyl | 0.25 + 1 | 1:4 | 50 | 11 |
| 172 | [I-110] + captan | 0.25 + 1 | 1:4 | 64 | 16 |
| 173 | [I-110] + metiram | 1 + 4 | 1:4 | 84 | 63 |
| 174 | [I-110] + flubenthiavalicarb | 0.063 + 0.25 | 1:4 | 98 | 69 |
| 175 | [I-110] + fenamidone | 0.016 + 0.063 | 1:4 | 72 | 41 |
| 176 | [I-110] + enestroburin | 0.25 + 1 | 1:4 | 99 | 38 |
| 177 | [I-110] + oxadixyl | 0.25 + 1 | 1:4 | 48 | 5 |
| 178 | [I-110] + tebuconazole | 0.25 + 1 | 1:4 | 88 | 13 |
| 179 | [I-110] + propiconazole | 0.25 + 1 | 1:4 | 75 | 6 |
| 180 | [I-110] + cyproconazole | 1 + 4 | 1:4 | 76 | 62 |
| 181 | [I-110] + flusilazole | 1 + 4 | 1:4 | 84 | 63 |
| 182 | [I-110] + boscalid | 0.25 + 1 | 1:4 | 73 | 7 |
| 183 | [I-110] + [B-6] | 0.25 + 0.25 | 1:1 | 48 | 15 |
| 184 | [I-110] + trifloxystrobin | 0.25 + 0.25 | 1:1 | 66 | 36 |
| 185 | [I-110] + mandipropamid | 0.63 + 0.63 | 1:1 | 76 | 12 |
| 186 | [I-110] + fluoxastrobin | 0.63 + 0.63 | 1:1 | 93 | 4 |
| 187 | [I-110] + azoxystrobin | 0.63 + 0.63 | 1:1 | 85 | 23 |
| 188 | [I-110] + pyraclostrobin | 0.63 + 0.63 | 1:1 | 55 | 16 |
| 189 | [I-113] + prochloraz | 4 + 16 | 1:4 | 99 | 40 |
| 190 | [I-113] + oxadixyl | 4 + 16 | 1:4 | 63 | 46 |
| 191 | [I-113] + ofurace | 4 + 16 | 1:4 | 68 | 48 |
| 192 | [I-113] + propiconazole | 4 + 16 | 1:4 | 93 | 43 |
| 193 | [I-113] + fluquinconazole | 1 + 4 | 1:4 | 71 | 7 |
| 194 | [I-113] + trifloxystrobin | 0.25 + 0.25 | 1:1 | 51 | 35 |
| 195 | [I-113] + mandipropamid | 0.25 + 0.25 | 1:1 | 93 | 42 |
| 196 | [I-113] + fluoxastrobin | 0.25 + 0.25 | 1:1 | 95 | 5 |
| 197 | [I-113] + pyraclostrobin | 0.25 + 0.063 | 4:1 | 96 | 60 |
| 198 | [I-120] + captan | 0.25 + 1 | 1:4 | 89 | 17 |
| 199 | [I-120] + benthiavalicarb | 0.063 + 0.25 | 1:4 | 98 | 64 |
| 200 | [I-120] + fenamidone | 0.016 + 0.063 | 1:4 | 72 | 40 |

-continued

| No. | Active compound/active compound combination | Conc. (mg/l) | Ratio | Observed activity (%) | Calculated activity according to Colby (%) |
|---|---|---|---|---|---|
| 201 | [I-120] + flusilazole | 0.25 + 1 | 1:4 | 89 | 6 |
| 202 | [I-120] + fluquinconazole | 0.25 + 1 | 1:4 | 71 | 6 |
| 203 | [I-120] + [D-8] | 0.25 + 1 | 1:4 | 79 | 46 |
| 204 | [I-120] + fluoxastrobin | 0.063 + 0.063 | 1:1 | 95 | 3 |
| 205 | [I-120] + azoxystrobin | 0.063 + 0.063 | 1:1 | 92 | 23 |
| 206 | [I-120] + pyraclostrobin | 0.063 + 0.016 | 4:1 | 54 | 16 |
| 207 | [I-180] + metiram | 1 + 4 | 1:4 | 57 | 24 |
| 208 | [I-180] + flubenthiavalicarb | 0.063 + 0.25 | 1:4 | 95 | 69 |
| 209 | [I-180] + fenamidone | 0.016 + 0.063 | 1:4 | 62 | 40 |
| 210 | [I-180] + enestroburin | 0.25 + 1 | 1:4 | 96 | 40 |
| 211 | [I-180] + benalaxyl | 1 + 4 | 1:4 | 70 | 28 |
| 212 | [I-180] + oxadixyl | 1 + 4 | 1:4 | 95 | 18 |
| 213 | [I-180] + ofurace | 1 + 4 | 1:4 | 92 | 17 |
| 214 | [I-180] + difenoconazole | 1 + 4 | 1:4 | 86 | 37 |
| 215 | [I-180] + tebuconazole | 1 + 4 | 1:4 | 97 | 25 |
| 216 | [I-180] + propiconazole | 1 + 4 | 1:4 | 88 | 26 |
| 217 | [I-180] + [B-6] | 0.25 + 0.25 | 1:1 | 40 | 16 |
| 218 | [I-180] + trifloxystrobin | 0.25 + 0.25 | 1:1 | 60 | 38 |
| 219 | [I-180] + mandipropamid | 0.063 + 0.063 | 1:1 | 39 | 11 |
| 220 | [I-180] + azoxystrobin | 0.063 + 0.063 | 1:1 | 52 | 22 |
| 221 | [I-245] + fenamidone | 0.016 + 0.063 | 1:4 | 73 | 40 |
| 222 | [I-245] + fluazinam | 0.25 + 0.25 | 1:1 | 51 | 20 |
| 223 | [I-245] + mandipropamid | 0.063 + 0.063 | 1:1 | 51 | 10 |
| 224 | [I-245] + fluoxastrobin | 0.25 + 0.25 | 1:1 | 96 | 14 |
| 225 | [I-245] + azoxystrobin | 0.063 + 0.063 | 1:1 | 51 | 21 |
| 226 | [I-245] + pyraclostrobin | 0.25 + 0.063 | 4:1 | 94 | 64 |
| 227 | [I-290] + folpet | 0.25 + 1 | 1:4 | 45 | 6 |
| 228 | [I-290] + metiram | 4 + 16 | 1:4 | 80 | 51 |
| 229 | [I-290] + flubenthiavalicarb | 0.063 + 0.25 | 1:4 | 89 | 68 |
| 230 | [I-290] + [B-6] | 0.25 + 0.25 | 1:1 | 30 | 10 |
| 231 | [I-290] + fluoxastrobin | 0.25 + 0.25 | 1:1 | 95 | 2 |

Use Example 6

Activity Against the Gray Mold Pathogen *Botryis cinerea* in the Microtiter Test The stock solution is pipetted onto a microtiter plate (MTP) and diluted to the stated active compound concentration using a malt-based aqueous nutrient medium for fungi. An aqueous spore suspension of *Botrytis cinerea* was then added. The plates were placed in a water vapor-saturated chamber at temperatures of 18° C. Using an absorption photometer, the MTPs were measured at 405 nm on day 7 after the inoculation.

Evaluation was carried out analogously to example 5.

| No. | Active compound/active compound combination | Conc. (mg/l) | Ratio | Observed activity (%) | Calculated activity according to Colby (%) |
|---|---|---|---|---|---|
| 232 | Tab. 1; I-9 [I-9] | 0.25 | | | 8 |
| 233 | Tab. 1; I-18 [I-18] | 16 | | | 11 |
| | | 1 | | | 8 |
| | | 0.063 | | | 6 |
| 234 | Tab. 1; I-25 [I-25] | 0.25 | | | 5 |
| 235 | Tab. 1; I-28 [I-28] | 4 | | | 0 |
| 236 | Tab. 1; I-98 [I-98] | 1 | | | 5 |
| | | 0.25 | | | 4 |
| 237 | Tab. 1; I-101 [I-101] | 1 | | | 1 |
| 238 | Tab. 1; I-110 [I-110] | 0.25 | | | 18 |
| | | 0.063 | | | 8 |
| 239 | Tab. 1; I-120 [I-120] | 16 | | | 15 |
| | | 1 | | | 9 |
| | | 0.063 | | | 0 |
| 240 | Tab. 1; I-180 [I-180] | 0.25 | | | 13 |
| | | 0.016 | | | 3 |
| 241 | Tab. 1; I-245 [I-245] | 0.25 | | | 0 |
| 242 | Tab. 1; I-290 [I-290] | 1 | | | 4 |
| 243 | chlorothalonil | 1 | | | 55 |
| 244 | folpet | 1 | | | 2 |
| 245 | CuSO$_4$ | 63 | | | 0 |
| 246 | thiophanate-methyl | 0.25 | | | 12 |
| 247 | tebuconazole | 0.25 | | | 50 |
| 248 | flusilazole | 0.25 | | | 43 |

-continued

| No. | Active compound/active compound combination | Conc. (mg/l) | Ratio | Observed activity (%) | Calculated activity according to Colby (%) |
|---|---|---|---|---|---|
| 249 | fluquinconazole | 0.063 | | 22 | |
| 250 | prothioconazole | 4 | | 48 | |
| 251 | vinclozolin | 1 | | 21 | |
| 252 | zoxamide | 1 | | 55 | |
| 253 | [B-6] | 16 | | 53 | |
| 254 | fluazinam | 0.063 | | 50 | |
| 255 | [I-9] + chlorothalonil | 0.25 + 1 | 1:4 | 91 | 59 |
| 256 | [I-18] + thiophanate-methyl | 0.063 + 0.25 | 1:4 | 35 | 17 |
| 257 | [I-18] + flusilazole | 0.063 + 0.25 | 1:4 | 76 | 46 |
| 258 | [I-18] + prothioconazole | 1 + 4 | 1:4 | 99 | 52 |
| 259 | [I-18] + [B-6] | 16 + 16 | 1:1 | 81 | 58 |
| 260 | [I-25] + chlorothalonil | 0.25 + 1 | 1:4 | 99 | 57 |
| 261 | [I-25] + folpet | 0.25 + 1 | 1:4 | 61 | 7 |
| 262 | [I-28] + maneb | 4 + 16 | 1:4 | 69 | 15 |
| 263 | [I-98] + prothioconazole | 1 + 4 | 1:4 | 90 | 51 |
| 264 | [I-98] + vinclozolin | 0.25 + 1 | 1:4 | 68 | 25 |
| 265 | [I-101] + zoxamide | 1 + 1 | 1:1 | 69 | 55 |
| 266 | [I-110] + chlorothalonil | 0.25 + 1 | 1:4 | 93 | 63 |
| 267 | [I-110] + folpet | 0.25 + 1 | 1:4 | 50 | 20 |
| 268 | [I-110] + vinclozolin | 0.25 + 1 | 1:4 | 81 | 35 |
| 269 | [I-110] + fluazinam | 0.063 + 0.063 | 1:1 | 77 | 54 |
| 270 | [I-120] + CuSO$_4$ | 16 + 63 | 1:4 | 53 | 15 |
| 271 | [I-120] + tebuconazole | 0.063 + 0.25 | 1:4 | 67 | 50 |
| 272 | [I-120] + prothioconazole | 1 + 4 | 1:4 | 94 | 53 |
| 273 | [I-180] + chlorothalonil | 0.25 + 1 | 1:4 | 92 | 61 |
| 274 | [I-180] + folpet | 0.25 + 1 | 1:4 | 75 | 15 |
| 275 | [I-180] + fluquinconazole | 0.016 + 0.063 | 1:4 | 100 | 24 |
| 276 | [I-180] + vinclozolin | 0.25 + 1 | 1:4 | 89 | 31 |
| 277 | [I-180] + carbendazim | 0.016 + 0.016 | 1:1 | 36 | 15 |
| 278 | [I-245] + vinclozolin | 0.25 + 1 | 1:4 | 55 | 21 |
| 279 | [I-290] + prothioconazole | 1 + 4 | 1:4 | 88 | 51 |

Use Example 7

Activity Against the Rice Blast Pathogen *Pyricularia oryzae* in the Microtiter Test The stock solutions were mixed according to the ratio, pipetted onto a microtiter plate (MTP) and diluted to the stated active compound concentration using a malt-based aqueous nutrient medium for fungi. An aqueous spore suspension of *Pyricularia oryzae* was then added. The plates were placed in a water vapor-saturated chamber at temperatures of 18° C. Using an absorption photometer, the MTPs were measured at 405 nm on day 7 after the inoculation.

Evaluation was carried out analogously to example 5.

| No. | Active compound/active compound combination | Conc. (mg/l) | Ratio | Observed activity (%) | Calculated activity according to Colby (%) |
|---|---|---|---|---|---|
| 280 | Tab. 1; I-9 [I-9] | 1 | | 13 | |
| | | 0.25 | | 7 | |
| 281 | Tab. 1; I-18 [I-18] | 16 | | 29 | |
| | | 4 | | 18 | |
| | | 1 | | 15 | |
| | | 0.25 | | 15 | |
| 282 | Tab. 1; I-25 [I-25] | 1 | | 24 | |
| 283 | Tab. 1; I-28 [I-28] | 1 | | 13 | |
| | | 0.25 | | 12 | |
| 284 | Tab. 1; I-98 [I-98] | 16 | | 43 | |
| | | 4 | | 15 | |
| | | 1 | | 0 | |
| | | 0.25 | | 0 | |
| 285 | Tab. 1; I-101 [I-101] | 16 | | 25 | |
| | | 4 | | 16 | |
| | | 1 | | 15 | |
| 286 | Tab. 1; I-110 [I-110] | 16 | | 8 | |
| 287 | Tab. 1; I-113 [I-113] | 4 | | 7 | |
| 288 | Tab. 1; I-120 [I-120] | 16 | | 25 | |
| 289 | Tab. 1; I-180 [I-180] | 1 | | 15 | |
| 290 | Tab. 1; I-245 [I-245] | 16 | | 23 | |
| | | 0.25 | | 10 | |
| 291 | fosetyl-Al | 16 | | 49 | |
| 292 | captan | 1 | | 44 | |
| 293 | maneb | 4 | | 32 | |

-continued

| No. | Active compound/active compound combination | Conc. (mg/l) | Ratio | Observed activity (%) | Calculated activity according to Colby (%) |
|---|---|---|---|---|---|
| 294 | metiram | 4 | | 26 | |
| 295 | metalaxyl | 63 | | 2 | |
| 296 | CuSO$_4$ | 63 | | 0 | |
| 297 | cyproconazole | 4 | | 54 | |
| 298 | fluquinconazole | 4 | | 0 | |
| 299 | prothioconazole | 4 | | 11 | |
| 300 | boscalid | 63 | | 12 | |
| 301 | metrafenone | 63 | | 42 | |
| 302 | dodemorph | 16 | | 72 | |
| 303 | cymoxanil | 16 | | 12 | |
| 304 | carbendazim | 0.25 | | 20 | |
| 305 | iprodione | 4 | | 46 | |
| 306 | cyazofamid | 4 | | 23 | |
| 307 | [I-9] + captan | 0.25 + 1 | 1:4 | 85 | 48 |
| 308 | [I-9] + cyproconazole | 1 + 4 | 1:4 | 79 | 60 |
| 309 | [I-9] + fluquinconazole | 1 + 4 | 1:4 | 39 | 13 |
| 310 | [I-9] + prothioconazole | 1 + 4 | 1:4 | 91 | 23 |
| 311 | [I-18] + captan | 0.25 + 1 | 1:4 | 88 | 52 |
| 312 | [I-18] + maneb | 1 + 4 | 1:4 | 57 | 42 |
| 313 | [I-18] + cyproconazole | 1 + 4 | 1:4 | 86 | 61 |
| 314 | [I-18] + fluquinconazole | 1 + 4 | 1:4 | 47 | 15 |
| 315 | [I-18] + iprodione | 4 + 4 | 1:1 | 89 | 55 |
| 316 | [I-18] + cyazofamid | 16 + 4 | 4:1 | 61 | 45 |
| 317 | [I-25] + maneb | 1 + 4 | 1:4 | 80 | 49 |
| 318 | [I-25] + prothioconazole | 1 + 4 | 1:4 | 100 | 33 |
| 319 | [I-28] + captan | 0.25 + 1 | 1:4 | 73 | 51 |
| 320 | [I-28] + prothioconazole | 1 + 4 | 1:4 | 50 | 23 |
| 321 | [I-98] + maneb | 1 + 4 | 1:4 | 58 | 32 |
| 322 | [I-98] + metiram | 1 + 4 | 1:4 | 47 | 26 |
| 323 | [I-98] + metalaxyl | 16 + 63 | 1:4 | 63 | 44 |
| 324 | [I-98] + boscalid | 16 + 63 | 1:4 | 65 | 49 |
| 325 | [I-98] + dodemorph | 4 + 16 | 1:4 | 98 | 76 |
| 326 | [I-98] + cymoxanil | 16 + 16 | 1:1 | 79 | 50 |
| 327 | [I-98] + carbendazim | 0.25 + 0.25 | 1:1 | 75 | 20 |

| No. | Active compound/active compound combination | Conc. (mg/l) | Ratio | Observed activity (%) | Calculated activity according to Colby (%) |
|---|---|---|---|---|---|
| 328 | [I-98] + cyazofamid | 16 + 4 | 4:1 | 93 | 56 |
| 329 | [I-101] + fosetyl-Al | 4 + 16 | 1:4 | 74 | 59 |
| 330 | [I-101] + CuSO$_4$ | 16 + 63 | 1:4 | 56 | 25 |
| 331 | [I-101] + fluquinconazole | 1 + 4 | 1:4 | 46 | 15 |
| 332 | [I-101] + prothioconazole | 1 + 4 | 1:4 | 64 | 25 |
| 333 | [I-101] + iprodione | 4 + 4 | 1:1 | 89 | 54 |
| 334 | [I-101] + cyazofamid | 4 + 1 | 4:1 | 91 | 22 |
| 335 | [I-110] + metrafenone | 16 + 63 | 1:4 | 100 | 47 |
| 336 | [I-113] + iprodione | 4 + 4 | 1:1 | 70 | 49 |
| 337 | [I-120] + cyazofamid | 16 + 4 | 4:1 | 64 | 42 |
| 338 | [I-180] + prothioconazole | 1 + 4 | 1:4 | 92 | 24 |
| 339 | [I-245] + captan | 0.25 + 1 | 1:4 | 90 | 49 |
| 340 | [I-245] + metrafenone | 16 + 63 | 1:4 | 100 | 55 |

Use Example 8

Activity Against the Speckled Leaf Blotch Pathogen *Septoria tritici* in the Microtiter Test The stock solution was mixed according to the ratio, pipetted onto a microtiter plate (MTP) and diluted to the stated active compound concentration using a malt-based aqueous nutrient medium for fungi. An aqueous spore suspension of *Septoria tritici* was then added. The plates were placed in a water vapor-saturated chamber at temperatures of 18° C. Using an absorption photometer, the MTPs were measured at 405 nm on day 7 after the inoculation.

Evaluation was carried out analogously to example 5.

| No. | Active compound/active compound combination | Conc. (mg/l) | Ratio | Observed activity (%) | Calculated activity according to Colby (%) |
|---|---|---|---|---|---|
| 341 | Tab. 1; I-120 [I-120] | 0.063 | | 0 | |
| 342 | prohexadione-Ca | 0.25 | | 5 | |
| 343 | [I-120] + prohexadione-Ca | 0.063 + 0.25 | 1:4 | 44 | 5 |

The test results show that, by virtue of the synergism, the mixtures according to the invention are considerably more effective than had been predicted using Colby's formula.

The invention claimed is:

1. A fungicidal mixture comprising, as active components:
   1) a compound (I) of 5-ethyl-6-octyl-[1,2,4]triazolo[1,5-a]pyrimidin-7-ylamine;
   and
   2) at least one active compound (II) of dimethomorph,
   wherein the compound (I) and the at least one active compound (II) of the mixture are present in a synergistically effective amount.

2. The fungicidal mixture of claim 1, wherein the weight ratio of the compound (I) and the compound (II) is from 100:1 to 1:100.

3. A composition comprising
   a liquid or solid carrier; and
   a mixture of
      1) a compound (I) 5-ethyl-6-octyl-[1,2,4]triazolo[1,5-a]pyrimidin-7-ylamine;
   and
      2) at least one active compound (II) of dimethomorph,
      wherein the compound (I) and the at least one active compound (II) of the mixture are present in a synergistically effective amount.

4. A method for controlling phytopathogenic harmful fungi comprising
   treating fungi, their habitat, or plants to be protected against fungal attack, soil or seed with an effective amount of
   1) a compound (I) of 5-ethyl-6-octyl-[1,2,4]triazolo[1,5-a]pyrimidin-7-ylamine;
   and
   2) at least one active compound (II) of dimethomorph,
   wherein the compound (I) and the at least one active compound (II) of the mixture are present in a synergistically effective amount;
   wherein the phytopathogenic harmful fungi are controlled.

5. The method of claim 4, wherein the weight ratio of the compound (I) and the at least one active compound (II) is from 100:1 to 1:100.

6. The method of claim 4, wherein the compound (I) and the at least one active compound (II) are applied simultaneously, separately, or in succession.

7. The method of claim 4, wherein the compound (I) and the at least one active compound (II) are applied in an amount of from 5 g/ha to 2000 g/ha.

8. The method of claim 4, wherein the compound (I) and the at least one active compound (II) are applied in an amount of from 1 g to 1000 g/100 kg of seed.

9. The method of claim 4, wherein harmful fungi from the class of Oomycetes are controlled.

10. Seed, comprising a mixture of
    1) a compound (I) of 5-ethyl-6-octyl-[1,2,4]triazolo[1,5-a]pyrimidin-7-ylamine;
    and
    2) at least one active compound (II) of dimethomorph,
    wherein the compound (I) and the at least one active compound (II) of the mixture are present in a synergistically effective amount;
    in an amount of from 1 to 1000 g/100 kg of seed.

11. A process for preparing a composition comprising contacting liquid or solid carriers with a mixture of
    1) a compound (I) selected from the group consisting of 5ethyl-6-octyl-[1,2,4]triazolo[1,5-a]pyrimidin-7-ylamine;
    and
    2) at least one active compound (II) of dimethomorph,
    wherein the compound (I)and the at least one active compound (II) of the mixture are present in a synergistically effective amount;
    wherein a composition is prepared.

* * * * *